United States Patent
Chen et al.

(10) Patent No.: US 12,415,810 B2
(45) Date of Patent: Sep. 16, 2025

(54) 2'-ISOPROPYL-SPIRO (3,3'-PYRROLIDINE OXINDOLE) LIVER X RECEPTOR REGULATOR, PREPARATION METHOD THEREFOR, AND USE THEREOF

(71) Applicant: SHENZHEN CELL INSPIRE PHARMACEUTICAL DEVELOPMENT CO., LTD., Guangdong (CN)

(72) Inventors: Ziyang Chen, Guangdong (CN); Qiong Gu, Guangdong (CN); Hao Chen, Guangdong (CN); Jun Xu, Guangdong (CN)

(73) Assignee: SHENZHEN CELL INSPIRE PHARMACEUTICAL DEVELOPMENT CO., LTD., Guangdong (CN)

( * ) Notice: Subject to any disclaimer, the term of this patent is extended or adjusted under 35 U.S.C. 154(b) by 841 days.

(21) Appl. No.: 17/577,018

(22) Filed: Jan. 17, 2022

(65) Prior Publication Data

US 2022/0135579 A1    May 5, 2022

Related U.S. Application Data

(63) Continuation of application No. PCT/CN2020/083073, filed on Apr. 2, 2020.

(30) Foreign Application Priority Data

Jul. 18, 2019 (CN) .......................... 201910652093.9

(51) Int. Cl.

| | | |
|---|---|---|
| A61P 3/00 | (2006.01) | |
| A61K 31/407 | (2006.01) | |
| A61K 45/06 | (2006.01) | |
| A61P 1/16 | (2006.01) | |
| A61P 3/04 | (2006.01) | |
| A61P 3/06 | (2006.01) | |
| A61P 3/10 | (2006.01) | |
| A61P 9/10 | (2006.01) | |
| A61P 17/00 | (2006.01) | |
| A61P 19/02 | (2006.01) | |
| A61P 19/10 | (2006.01) | |
| A61P 25/16 | (2006.01) | |
| A61P 25/28 | (2006.01) | |
| A61P 35/00 | (2006.01) | |
| C07D 487/10 | (2006.01) | |

(52) U.S. Cl.
CPC .......... *C07D 487/10* (2013.01); *A61K 31/407* (2013.01); *A61K 45/06* (2013.01); *A61P 3/06* (2018.01)

(58) Field of Classification Search
None
See application file for complete search history.

(56) References Cited

U.S. PATENT DOCUMENTS

| | | | | |
|---|---|---|---|---|
| 5,948,807 A | * | 9/1999 | Efange | C07D 209/96 548/410 |
| 7,550,499 B2 | * | 6/2009 | Tuerdi | C07D 471/10 548/452 |
| 7,728,008 B2 | * | 6/2010 | Qiao | C07D 401/04 546/244 |

FOREIGN PATENT DOCUMENTS

| | | | |
|---|---|---|---|
| CN | 1950365 A | 4/2007 | |
| CN | 106008532 A | 10/2016 | |
| CN | 108707101 A | * 10/2018 | ........... C07D 209/34 |
| CN | 110305141 A | * 10/2019 | ........... A61K 31/407 |
| CN | 110330498 A | 10/2019 | |
| JP | 2007536252 A | 12/2007 | |
| JP | 2010501578 A | 1/2010 | |
| WO | 2008024497 A2 | 2/2008 | |
| WO | 2010138598 A2 | 12/2010 | |
| WO | 2014085453 A2 | 6/2014 | |
| WO | 2015035015 A1 | 3/2015 | |
| WO | 2016100619 A2 | 6/2016 | |

(Continued)

OTHER PUBLICATIONS

Nakazaki et al., Chem. Asian J. 2016, 11, 3267-32 (Year: 2016).*

(Continued)

*Primary Examiner* — Kortney L. Klinkel
*Assistant Examiner* — Alison Azar Salamatian

(57) ABSTRACT

Provided is a liver X receptor regulator of spiro(3,3'-isopropylpyrrolidine oxindole), as well as a preparation method and use thereof. Specifically, a compound is provided, which is a compound represented by Formula (I); or a stereoisomer, geometric isomer, tautomer, nitrogen oxide, hydrate, solvate, metabolite, pharmaceutically acceptable salt, or prodrug of the compound represented by Formula (I).

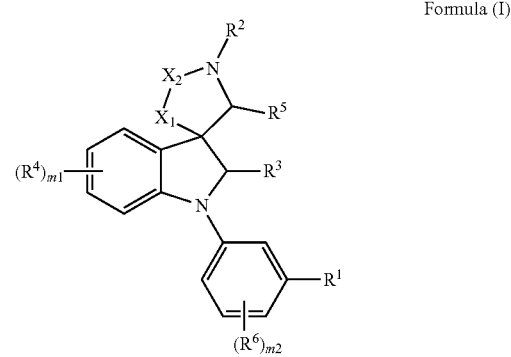

Formula (I)

18 Claims, 3 Drawing Sheets

(56) References Cited

FOREIGN PATENT DOCUMENTS

WO     WO-2019169257 A1 *   9/2019   ......... C07D 471/10
WO         2021008014 A1     1/2021

OTHER PUBLICATIONS

English Translation CN 108707101 (Year: 2018).*
Qiao et al., J. Med. Chem. 2013, 56, 22, 9275-9295 (Year: 2013).*
The extended European search report in European Patent Application No. 20841629.7, dated Jun. 28, 2022.
Notice of Reasons for Refusal in Japanese Patent Application No. 2022-503560, dated Feb. 7, 2023.
Communication under Rule 71(3) EPC in European Patent Application No. 20 841 629.7, dated Feb. 28, 2023.
Atsuo Nakazaki et al., "Diastereoselective synthesis of 3,3-disubstituted oxindoles from atropisomeric N-aryl oxindole derivatives", Tetrahedron Letters, 53 (2012) 7131-7134.

* cited by examiner

2'-ISOPROPYL-SPIRO (3,3'-PYRROLIDINE OXINDOLE) LIVER X RECEPTOR REGULATOR, PREPARATION METHOD THEREFOR, AND USE THEREOF

CROSS-REFERENCE TO RELATED APPLICATIONS

This application is a continuation of International Application No. PCT/CN2020/083073, filed on Apr. 2, 2020, which claims priority to Chinese Patent Application No. 201910652093.9, filed on Jul. 18, 2019. The disclosures of the aforementioned applications are hereby incorporated by reference in their entireties.

FIELD

The present disclosure relates to the field of biomedicines. Specifically, the present disclosure relates to a 2'-isopropyl-spiro (3,3'-pyrrolidine oxindole) liver X receptor regulator, a preparation method therefor, and uses thereof.

BACKGROUND

Liver X receptor (LXR) is a ligand-dependent transcription factor that usually forms a heterodimer in a form of LXR/RXR together with retinol X receptor (RXR). Under the premise of ligand activation, LXR can be bonded to an LXR response element (LXRE) on the target gene to regulate a transcription process of the target gene. LXR includes two subtypes, i.e., LXRα and LXRβ. LXRα is distributed in liver, small intestine, adipose tissue, and macrophages with immune functions, while LXRβ is widely distributed throughout the body.

LXR is a nuclear receptor activated by oxysterols, and plays an important role in fat, cholesterol, and sugar metabolisms, and inflammation. It has broad development prospects to develop new drugs targeting at LXR. The synthetic LXR agonists include GW3965 and TO901317, etc. The LXR agonists can be developed and used as lead compounds for the treatment of atherosclerosis, cancer, Alzheimer's disease, atopic dermatitis, and other diseases.

At present, there are few LXR antagonists or inverse agonists, mainly including SR9243, SR9238, PP2P, fenofibrate, morin, and luteolin, etc. Many articles have indicated that LXR antagonists or inverse agonists have strong anti-fatty liver activity. Among them, the mechanism of LXR antagonists or inverse agonists for lipid-lowering is to down-regulate sterol regulatory element-binding protein (SREBP-1c) of LXR target gene, acetyl-coA carboxylase (ACC), lipase (FAS), and stearoyl-CoA desaturase-1 (SCD-1), so as to reduce triglyceride synthesis. In addition, SR9243 can also produce broad-spectrum anti-tumor effects by inhibiting glycolysis and lipogenesis in tumor cells. The LXR antagonists or inverse agonists can be developed and used as lead compounds for the treatment of hyperlipoidemia, fatty liver, obesity, diabetes, metabolic syndrome, and targeted tumor energy metabolism.

SUMMARY

The present disclosure is based on the following facts and problems that are found and recognized by the applicant.

Through a large number of experimental studies, a new liver X receptor regulator is provided. The applicant surprisingly found that it has a significant regulatory activity for liver X receptors. The new liver X receptor regulator can be effectively used to treat or prevent hyperlipidemia, fatty liver, obesity, diabetes, metabolic syndrome, or used to target at tumor energy metabolism, and also has significant therapeutic effects for cancers such as glioblastoma, atherosclerosis, dyslipidemia, metabolic syndrome, Parkinson's disease, Alzheimer's disease, multiple sclerosis, atopic dermatitis, rheumatoid arthritis and osteoporosis, having broad application prospects.

In a first aspect of the present disclosure, the present disclosure provides a compound. The compound is a compound represented by formula (I), or the compound is a stereoisomer, geometric isomer, tautomer, nitrogen oxide, hydrate, solvate, metabolite, pharmaceutically acceptable salt, or prodrug of the compound represented by formula (I),

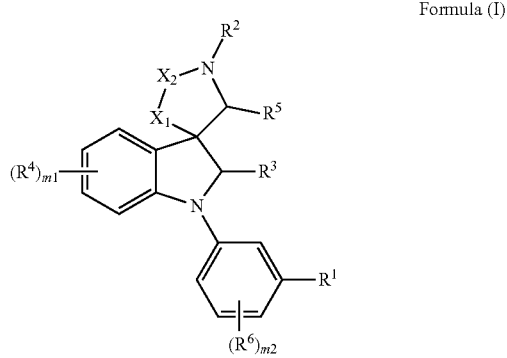

Formula (I)

in which:

$X_1$, $X_2$ are independently $C(R^{7a})_2$, O, S, or $NR^8$;

$R^1$ is H, D, F, Cl, Br, I, —CN, —NO$_2$, —OH, —NH$_2$, —COOH, $C_{1-6}$ alkyl, $C_{2-6}$ alkenyl, $C_{2-6}$ alkynyl, $C_{3-8}$ cycloalkyl, $C_{1-6}$ halogenated alkyl, $C_{1-6}$ hydroxyl-substituted alkyl, $C_{1-6}$ alkoxyl, $C_{1-6}$ halogenated alkoxyl, —C(=O)R$^{7b}$, —C(=O)OR$^{7b}$, —OC(=O)R$^{7b}$, —C(=O)NR$^{8a}$R$^{8b}$, —NR$^8$C(=O)R$^{7b}$, R$^{8a}$R$^{8b}$N—S(=O)$_2$—, —R$^8$N—S(=O)$_2$R$^{7b}$, R$^{7b}$S(=O)$_2$—, $C_{6-11}$) aryl, or heteroaryl consisting of 5-12 atoms, wherein one, two, three, four or five carbon atoms of the $C_{6-10}$ aryl or heteroaryl consisting of 5-12 atoms are independently and optionally substituted with $R^{10}$;

each $R^{10}$ is each independently H, D, F, Cl, Br, I, —CN, —NO$_2$, —OH, —NH$_2$, —COOH, $C_{1-6}$ alkyl, $C_{2-6}$ alkenyl, $C_{2-6}$ alkynyl, $C_{3-8}$ cycloalkyl, $C_{1-6}$ halogenated alkyl, $C_{1-6}$ hydroxyl-substituted alkyl, $C_{1-6}$ alkoxyl, $C_{1-6}$ halogenated alkoxyl, —C(=O)R$^{7b}$, —C(=O)OR$^{7b}$, —OC(=O)R$^{7b}$, —C(=O)NR$^{8a}$R$^{8b}$, —NR$^8$C(=O)R$^{7b}$, R$^{8a}$R$^{8b}$N—S(=O)$_2$—, —R$^8$N—S(=O)$_2$R$^{7b}$, or R$^{7b}$S(=O)$_2$—;

$R^2$ is —C(=O)R$^{7c}$, —C(=O)(C(R$^{7a}$)$_2$)$_{n1}$R$^{7c}$, —C(=O)OR$^{7c}$, —OC(=O)R$^{7c}$, —C(=O)NR$^{8a}$R$^{8b}$, —C(=S)NR$^{8a}$R$^{8b}$, —NR$^8$C(=O)R$^{7c}$, R$^{8a}$R$^{8b}$N—S(=O)$_2$—, —R$^8$N—S(=O)$_2$R$^{7c}$, or R$^{7c}$S(=O)$_2$—;

$R^3$ is H, D, F, Cl, Br, I, —CN, —NO$_2$, —OH, —NH$_2$, —COOH, O, or $C_{1-6}$ alkyl;

$R^4$, $R^5$, and $R^6$ are each independently H, D, F, Cl, Br, I, —CN, —NO$_2$, —OH, —NH$_2$, —COOH, or $C_{1-6}$ alkyl;

$R^{7a}$, $R^{7b}$, $R^{7c}$, $R^8$, $R^{8a}$, and $R^{8b}$ are each independently H, D, F, Cl, Br, I, —CN, —NO$_2$, —OH, —NH$_2$, —COOH, $C_{1-6}$ alkyl, or $C_{1-6}$ halogenated alkyl; and m1, m2, and n1 are independently 0, 1, 2, 3, or 4.

According to an embodiment of the present disclosure, the compound may further have at least one of the following additional technical features.

According to an embodiment of the present disclosure, $R^1$ is H, D, F, Cl, Br, I, —CN, —NO$_2$, —OH, —NH$_2$, —COOH, $C_{1-6}$ alkyl, $C_{2-4}$ alkenyl, $C_{2-4}$ alkynyl, $C_{3-6}$ cycloalkyl, $C_{1-4}$ halogenated alkyl, $C_{1-4}$ hydroxyl-substituted alkyl, $C_{1-4}$ alkoxyl, $C_{1-4}$ halogenated alkoxyl, —C(=O)R$^{7b}$, —C(=O)OR$^{7b}$, —OC(=O)R$^{7b}$, —C(=O)NR$^{8a}$R$^{8b}$, —NR$^8$C(=O)R$^{7b}$, R$^{8a}$R$^{8b}$N—S(=O)$_2$—, —R$^8$N—S(=O)$_2$R$^{7b}$, R$^{7b}$S(=O)$_2$—, $C_{6-10}$ aryl, or heteroaryl consisting of 5-10 atoms, where one, two, three, four or five carbon atoms of the $C_{6-10}$ aryl or heteroaryl consisting of 5-10 atoms are independently and optionally substituted with R$^{10}$; and R$^{10}$ is each independently H, D, F, Cl, Br, I, —CN, —NO$_2$, —OH, —NH$_2$, —COOH, $C_{1-4}$ alkyl, $C_{2-4}$ alkenyl, $C_{2-4}$ alkynyl, $C_{3-6}$ cycloalkyl, $C_{1-4}$ halogenated alkyl, $C_{1-4}$ hydroxyl-substituted alkyl, $C_{1-4}$ alkoxyl, $C_{1-4}$ halogenated alkoxyl, —C(=O)R$^{7b}$, —C(=O)OR$^{7b}$, —OC(=O)R$^{7b}$, —C(=O)NR$^{8a}$R$^{8b}$, —NR$^8$C(=O)R$^{7b}$, R$^{8a}$R$^{8b}$N—S(=O)$_2$—, —R$^8$N—S(=O)$_2$R$^{7b}$, or R$^{7b}$S(=O)$_2$—.

According to an embodiment of the present disclosure, $R^1$ is H, D, F, Cl, Br, I, —CN, —NO$_2$, —OH, —NH$_2$, —COOH, methyl, ethyl, n-propyl, isopropyl, tert-butyl, n-butyl, trifluoromethyl, 1-chloroethyl, difluoromethyl, 2-fluoroethyl, 3,3,3-trifluoropropyl, hydroxymethyl, 1-hydroxyethyl, dihydroxymethyl, 2-hydroxyethyl, 3,3,3-trihydroxypropyl, —C(=O)R$^{7b}$, —C(=O)OR$^{7b}$, —OC(=O)R$^{7b}$, —C(=O)NR$^{8a}$R$^{8b}$, —NR$^8$C(=O)R$^{7b}$, R$^{8a}$R$^{8b}$N—S(=O)$_2$—, —R$^8$N—S(=O)$_2$R$^{7b}$, R$^{7b}$S(=O)$_2$—, $C_{6-10}$ aryl, or heteroaryl consisting of 5-10 atoms, where one, two, three, four or five carbon atoms of the $C_{6-10}$ aryl or heteroaryl consisting of 5-10 atoms are independently and optionally substituted with R$^{10}$; and R$^{10}$ is each independently H, D, F, Cl, Br, I, —CN, —NO$_2$, —OH, —NH$_2$, —COOH, methyl, ethyl, n-propyl, isopropyl, tert-butyl, n-butyl, trifluoromethyl, 1-chloroethyl, difluoromethyl, 2-fluoroethyl, 3,3,3-trifluoropropyl, hydroxymethyl, 1-hydroxyethyl, dihydroxymethyl, 2-hydroxyethyl, 3,3,3-trihydroxypropyl, —C(=O)R$^{7b}$, —C(=O)OR$^{7b}$, —OC(=O)R$^{7b}$, —C(=O)NR$^{8a}$R$^{8b}$, —NR$^8$C(=O)R$^{7b}$, R$^{8a}$R$^{8b}$N—S(=O)$_2$—, —R$^8$N—S(=O)$_2$R$^{7b}$, or R$^{7b}$S(=O)$_2$—.

According to an embodiment of the present disclosure, $R^4$, $R^5$, and $R^6$ are each independently H, D, F, Cl, Br, I, —CN, —NO$_2$, —OH, —NH$_2$, —COOH, or $C_{1-4}$ alkyl; and R$^{7a}$, R$^{7b}$, R$^{7c}$, R$^8$, R$^{8a}$, and R$^{8b}$ are each independently H, D, F, Cl, Br, I, —CN, —NO$_2$, —OH, —NH$_2$, —COOH, $C_{1-4}$ alkyl, or $C_{1-4}$ halogenated alkyl.

According to an embodiment of the present disclosure, $R^4$, $R^5$, and $R^6$ are independently H, D, F, Cl, Br, I, —CN, —NO$_2$, —OH, —NH$_2$, —COOH, methyl, ethyl, n-propyl, isopropyl, tert-butyl, or n-butyl; and R$^{7a}$, R$^{7b}$, R$^{7c}$, R$^8$, R$^{8a}$, and R$^{8b}$ are each independently H, D, F, Cl, Br, I, —CN, —NO$_2$, —OH, —NH$_2$, —COOH, methyl, ethyl, n-propyl, isopropyl, tert-butyl, n-butyl, trifluoromethyl, 1-chloroethyl, difluoromethyl, 2-fluoroethyl, or 3,3,3-trifluoropropyl.

According to an embodiment of the present disclosure, the compound is a compound represented by Formula (II-1) or Formula (II-2); or the compound is a stereoisomer, geometric isomer, tautomer, nitrogen oxide, hydrate, solvate, metabolite, pharmaceutically acceptable salt, or prodrug of the compound represented by Formula (II-1) or Formula (II-2),

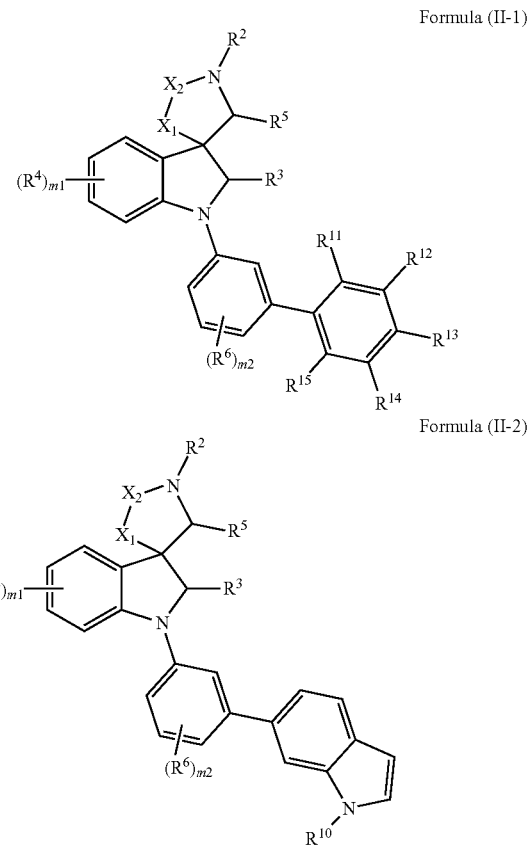

in which:

R$^{11}$, R$^{12}$, R$^{13}$, R$^{14}$, or R$^{15}$ is independently H, D, F, Cl, Br, I, —CN, —NO$_2$, —OH, —NH$_2$, —COOH, $C_{1-6}$ alkyl, $C_{2-6}$ alkenyl, $C_{2-6}$ alkynyl, $C_{3-8}$ cycloalkyl, $C_{1-6}$ halogenated alkyl, $C_{1-6}$ hydroxyl-substituted alkyl, $C_{1-6}$ alkoxyl, $C_{1-6}$ halogenated alkoxyl, —C(=O)R$^{7b}$, —C(=O)OR$^{7b}$, —OC(=O)R$^{7b}$, —C(=O)NR$^{8a}$R$^{8b}$, —NR$^8$C(=O)R$^m$, R$^{8a}$R$^{8b}$N—S(=O)$_2$—, —R$^8$N—S(=O)$_2$R$^{7b}$, or R$^{7b}$S(=O)$_2$—.

According to an embodiment of the present disclosure, R$^{11}$, R$^{12}$, R$^{13}$, R$^{14}$ or R$^{15}$ is independently H, D, F, Cl, Br, I, —CN, —NO$_2$, —OH, —NH$_2$, —COOH, $C_{1-4}$ alkyl, $C_{2-4}$ alkenyl, $C_{2-4}$ alkynyl, $C_{3-6}$ cycloalkyl, $C_{1-4}$ halogenated alkyl, $C_{1-4}$ hydroxyl-substituted alkyl, $C_{1-4}$ alkoxyl, $C_{1-4}$ halogenated alkoxyl, —C(=O)R$^{7b}$, —C(=O)OR$^{7b}$, —OC(=O)R$^{7b}$, —C(=O)NR$^{8a}$R$^{8b}$, —NR$^8$C(=O)R$^{7b}$, R$^{8a}$R$^{8b}$N—S(=O)$_2$—, —R$^8$N—S(=O)$_2$R$^{7b}$, or R$^{7b}$S(=O)$_2$—.

According to an embodiment of the present disclosure, R$^{11}$, R$^{12}$, R$^{13}$, R$^{14}$ or R$^{15}$ is independently H, D, F, Cl, Br, I, —CN, —NO$_2$, —OH, —NH$_2$, —COOH, methyl, ethyl, n-propyl, isopropyl, tert-butyl, n-butyl, trifluoromethyl, 1-chloroethyl, difluoromethyl, 2-fluoroethyl, 3,3,3-trifluoropropyl, hydroxymethyl, 1-hydroxyethyl, dihydroxymethyl, 2-hydroxyethyl, 3,3,3-trihydroxypropyl, —C(=O)R$^{7b}$, —C(=O)OR$^{7b}$, —OC(=O)R$^{7b}$, —C(=O)NR$^{8a}$R$^{8b}$, —NR$^8$C(=O)R$^{7b}$, R$^{8a}$R$^{8b}$N—S(=O)$_2$—, —R$^8$N—S(=O)$_2$R$^{7b}$, or R$^{7b}$S(=O)$_2$—.

According to an embodiment of the present disclosure, the compound is a compound represented by represented by Formula (II-1-A), (II-1-B), or (II-1-C); or the compound is a stereoisomer, geometric isomer, tautomer, nitrogen oxide, hydrate, solvate, metabolite, pharmaceutically acceptable salt, or prodrug of the compound represented by Formula (II-1-A), (II-1-B), or (II-1-C),

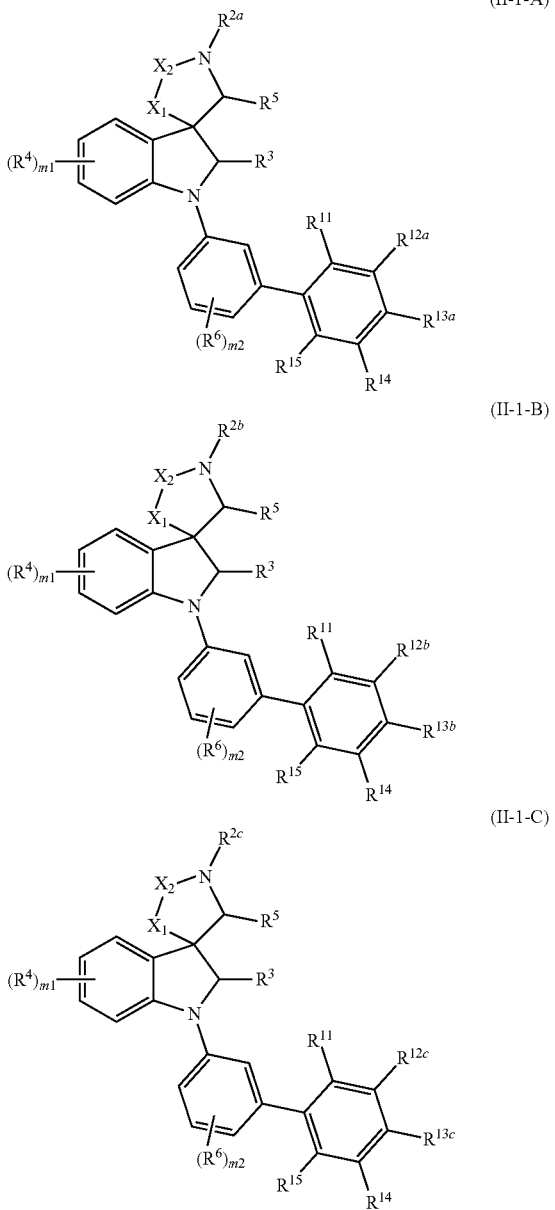

in which:
$R^{2a}$ is —C(═O)$R^{7c}$, —C(═O)(C($R^{7a}$)$_2$)$_{n1}R^{7c}$, —C(═O)O$R^{7c}$, —OC(═O)$R^{7c}$, or $R^{7c}$S(═O)$_2$—; $R^{12a}$ is $R^{7b}$S(═O)$_2$—; and $R^{13a}$ is H, D, F, Cl, Br, I, —CN, —NO$_2$, —OH, —NH$_2$, —COOH, $C_{1-6}$ alkyl, $C_{2-6}$ alkenyl, $C_{2-6}$ alkynyl, $C_{3-8}$ cycloalkyl, $C_{1-6}$ halogenated alkyl, $C_{1-6}$ hydroxyl-substituted alkyl, $C_{1-6}$ alkoxyl, or $C_{1-6}$ halogenated alkoxy;

$R^{2b}$ is R'S(═O)$_2$—; and $R^{12b}$ and $R^{13b}$ are each independently H, D, F, Cl, Br, I, —CN, —NO$_2$, —OH, —NH$_2$, —COOH, $C_{1-6}$ alkyl, $C_{2-6}$ alkenyl, $C_{2-6}$ alkynyl, $C_{3-8}$ cycloalkyl, $C_{1-6}$ halogenated alkyl, $C_{1-6}$ hydroxyl-substituted alkyl, $C_{1-6}$ alkoxyl, $C_{1-6}$ halogenated alkoxyl, —C(═O)$R^{7b}$, —C(═O)O$R^{7b}$, —OC(═O)$R^{7b}$, —C(═O)N$R^{8a}R^{8b}$, or —N$R^8$C(═O)$R^{7b}$; and $R^{2c}$ is —C(═O)$R^{7c}$, —C(═O)(C($R^{7a}$)$_2$)$_{n1}R^{7c}$, —C(═O)O$R^{7c}$, —OC(═O)$R^{7c}$, —C(═S)N$R^{8a}R^{8b}$, —C(═O)N$R^{8a}R^{8b}$, or —N$R^8$C(═O)$R^{7c}$; $R^{12c}$ is H, D, F, Cl, Br, I, —CN, —NO$_2$, —OH, —NH$_2$, —COOH, $C_{1-6}$ alkyl, $C_{2-6}$ alkenyl, $C_{2-6}$ alkynyl, $C_{3-8}$ cycloalkyl, $C_{1-6}$ halogenated alkyl, $C_{1-6}$ hydroxyl-substituted alkyl, $C_{1-6}$ alkoxyl, or $C_{1-6}$ halogenated alkoxy; and $R^{13c}$ is —C(═O)N$R^{8a}R^{8b}$, or —N$R^8$C(═O)$R^{7b}$.

The applicant found that the compound represented by Formula (II-1-A) or (II-1-B) can effectively inversely activate liver X receptors, effectively treat or prevent hyperlipidemia, fatty liver, obesity, diabetes or metabolism syndrome, or it can be used to target tumor energy metabolism. In addition, the applicant found that the compound represented by Formula (II-1-C) can effectively activate liver X receptors, and effectively treat or prevent glioblastoma, atherosclerosis, dyslipidemia, metabolic syndrome, Parkinson's disease, Alzheimer's disease, multiple sclerosis, atopic dermatitis, rheumatoid arthritis, osteoporosis drugs, or a combination thereof.

According to an embodiment of the present disclosure, $R^{2a}$ is —C(═O)$R^{7c}$, —C(═O)(C($R^{7a}$)$_2$)$_{n1}R^{7c}$, —C(═O)O$R^{7c}$, —OC(═O)$R^{7c}$, or $R^{7c}$S(═O)$_2$—; $R^{12a}$ is $R^{7b}$S(═O)$_2$—; and $R^{13a}$ is H, D, F, Cl, Br, I, —CN, —NO$_2$, —OH, —NH$_2$, —COOH, $C_{1-4}$ alkyl, $C_{2-4}$ alkenyl, $C_{2-4}$ alkynyl, $C_{3-6}$ cycloalkyl, $C_{1-4}$ halogenated alkyl, $C_{1-4}$ hydroxyl-substituted alkyl, $C_{1-4}$ alkoxyl, or $C_{1-4}$ halogenated alkoxy;

$R^{2b}$ is $R^{7c}$S(═O)$_2$—; and $R^{12b}$ and $R^{13b}$ are each independently H, D, F, Cl, Br, I, —CN, —NO$_2$, —OH, —NH$_2$, —COOH, $C_{1-4}$ alkyl, $C_{2-4}$ alkenyl, $C_{2-4}$ alkynyl, $C_{3-6}$ cycloalkyl, $C_{1-4}$ halogenated alkyl, $C_{1-4}$ hydroxyl-substituted alkyl, $C_{1-4}$ alkoxyl, $C_{1-4}$ halogenated alkoxyl, —C(═O)$R^{7b}$, —C(═O)O$R^{7b}$, —OC(═O)$R^{7b}$, —C(═O)N$R^{8a}R^{8b}$, or —N$R^8$C(═O)$R^{7b}$; and $R^{2c}$ is —C(═O)$R^{7c}$, —C(═O)(C($R^{7a}$)$_2$)$_{n1}R^{7c}$, —C(═O)O$R^{7c}$, —OC(═O)$R^{7c}$, —C(═S)N$R^{8a}R^{8b}$, —C(═O)N$R^{8a}R^{8b}$, or —N$R^8$C(═O)$R^{7c}$; $R^{12c}$ is H, D, F, Cl, Br, I, —CN, —NO$_2$, —OH, —NH$_2$, —COOH, $C_{1-4}$ alkyl, $C_{2-4}$ alkenyl, $C_{2-4}$ alkynyl, $C_{3-6}$ cycloalkyl, $C_{1-4}$ halogenated alkyl, $C_{1-4}$ hydroxyl-substituted alkyl, $C_{1-4}$ alkoxyl, or $C_{1-4}$ halogenated alkoxy; and $R^{13c}$ is —C(═O)N$R^{8a}R^{8b}$, or —N$R^8$C(═O)$R^{7b}$.

According to an embodiment of the present disclosure, $R^{2a}$ is —C(═O)$R^{7c}$, —C(═O)(C($R^{7a}$)$_2$)$_{n1}R^{7c}$, —C(═O)O$R^{7c}$, —OC(═O)$R^{7c}$, or $R^{7c}$S(═O)$_2$—; $R^{12a}$ is $R^{7b}$S(═O)$_2$—; and $R^{13a}$ is H, D, F, Cl, Br, I, —CN, —NO$_2$, —OH, —NH$_2$, —COOH, methyl, ethyl, n-propyl, isopropyl, tert-butyl, n-butyl, trifluoromethyl, 1-chloroethyl, difluoromethyl, 2-fluoroethyl, 3,3,3-trifluoropropyl, hydroxymethyl, 1-hydroxyethyl, dihydroxymethyl, 2-hydroxyethyl, or 3,3,3-trihydroxypropyl;

$R^{2b}$ is $R^{7c}$S(═O)$_2$—; and $R^{12b}$ and $R^{13b}$ are each independently H, D, F, Cl, Br, I, —CN, —NO$_2$, —OH, —NH$_2$, —COOH, methyl, ethyl, n-propyl, isopropyl, tert-butyl, n-butyl, trifluoromethyl, 1-chloroethyl, difluoromethyl, 2-fluoroethyl, 3,3,3-trifluoropropyl, hydroxymethyl, 1-hydroxyethyl, dihydroxymethyl, 2-hydroxyethyl, 3,3,3-trihydroxypropyl, —C(═O)$R^{7b}$, —C(═O)O$R^{7b}$, —OC(═O)$R^{7b}$, —C(═O)N$R^{8a}R^{8b}$, or —N$R^8$C(═O)$R^{7b}$; and $R^{2c}$ is —C(═O)$R^{7c}$, —C(═O)(C($R^{7a}$)$_2$)$_{n1}R^{7c}$, —C(═O)O$R^{7c}$, —OC(═O)$R^{7c}$, —C(═S)N$R^{8a}R^{8b}$, —C(═O)N$R^{8a}R^{8b}$, or —N$R^8$C(═O)$R^{7c}$; $R^{12c}$ is H, D, F, Cl, Br, I, —CN, —NO$_2$, —OH, —NH$_2$, —COOH, methyl, ethyl, n-propyl, isopropyl, tert-butyl, n-butyl, trifluoromethyl, 1-chloroethyl, difluoromethyl, 2-fluoroethyl, 3,3,3-trifluoropropyl, hydroxymethyl, 1-hydroxyethyl, dihydroxymethyl, 2-hydroxyethyl, 3,3,3-trihydroxypropyl; and $R^{13c}$ is —C(=O)NR$^{8a}$R$^{8b}$, or —NR$^8$C(=O)R$^{7b}$.

According to an embodiment of the present disclosure, the compound is a compound represented by Formula (II-1-A-a), (II-1-A-b), (II-1-B-a), (II-1-B-b), (II-1-C-a), or (II-1-C-b), or the compound is a stereoisomer, geometric isomer, tautomer, nitrogen oxide, hydrate, solvate, metabolite, pharmaceutically acceptable salt, or prodrug of the compound represented by Formula (II-1-A-a), (II-1-A-b), (II-1-B-a), (II-1-B-b), (II-1-C-a), or (II-1-C-b),

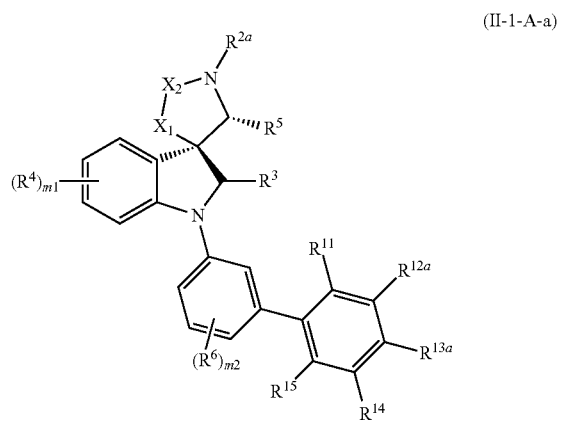

(II-1-A-a)

(II-1-A-b)

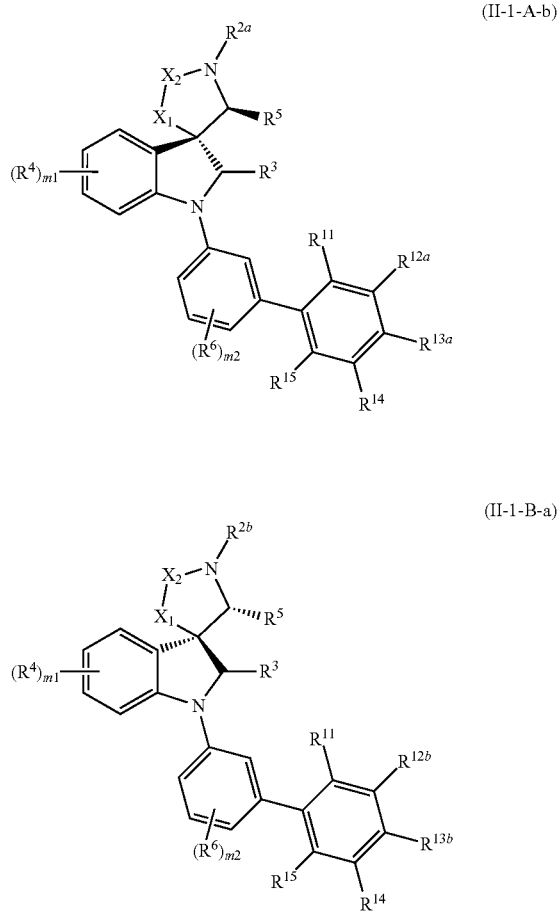

(II-1-B-a)

(II-1-B-b)

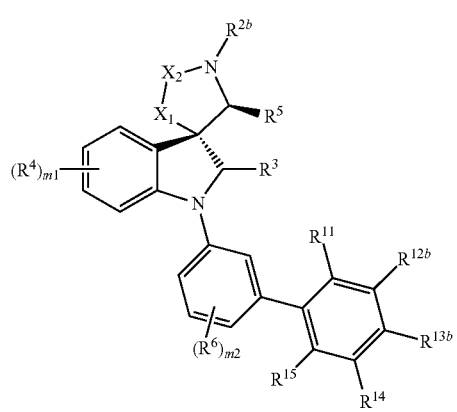

(II-1-C-a)

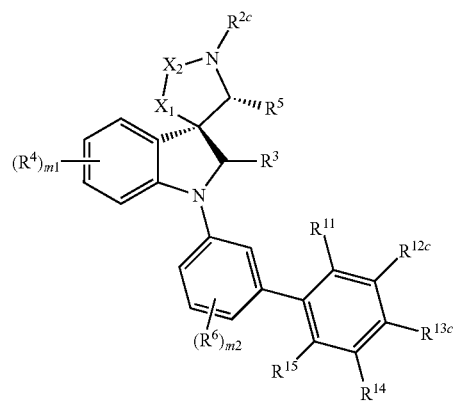

(II-1-C-b)

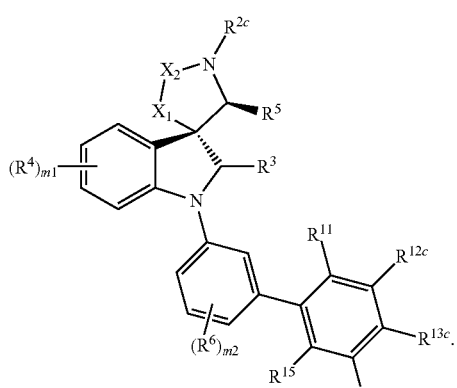

According to an embodiment of the present disclosure, the compound is a compound having one of the following structures, or the compound is a stereoisomer, geometric isomer, tautomer, nitrogen oxide, hydrate, solvate, metabolite, pharmaceutically acceptable salt, or prodrug of the compound having one of the following structures:

2a 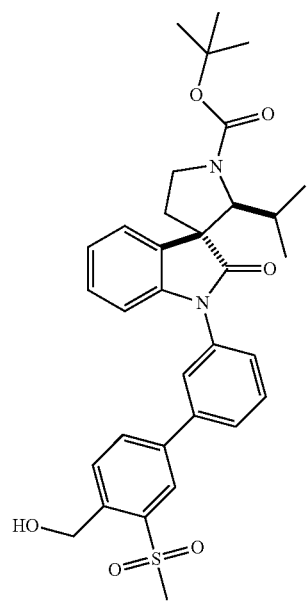
2a-2 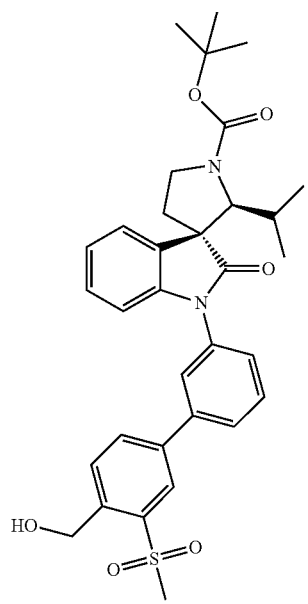
2b 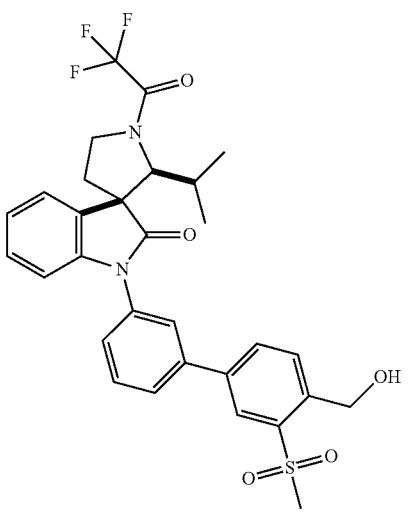
2a-1 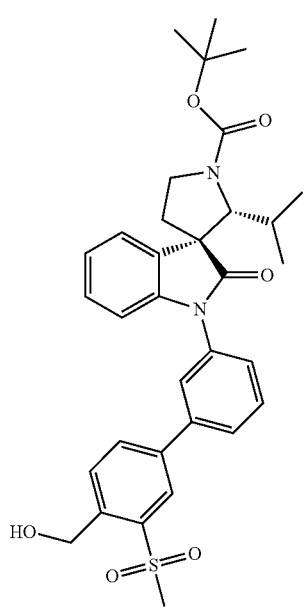
2c 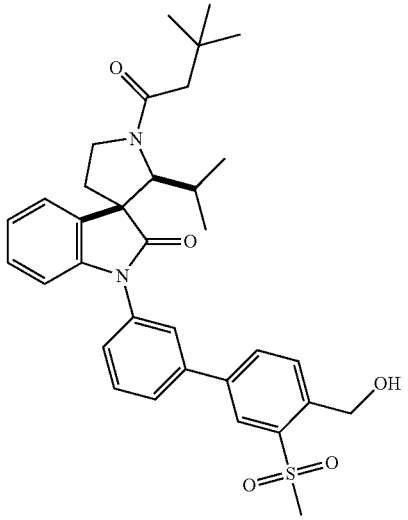

11
-continued
2d
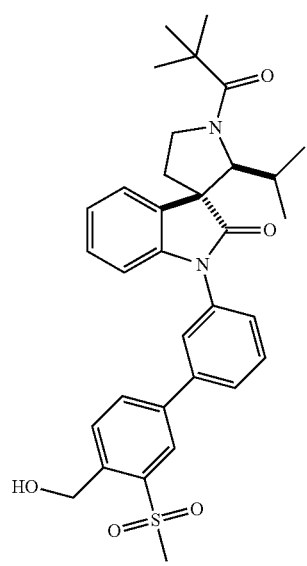
2e
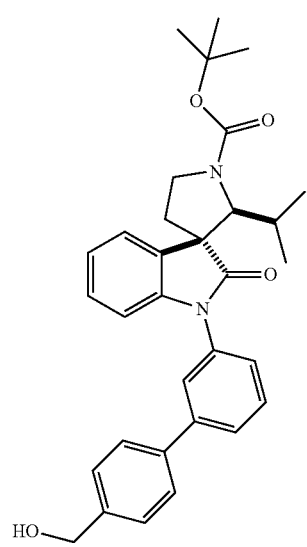
12
-continued
3a
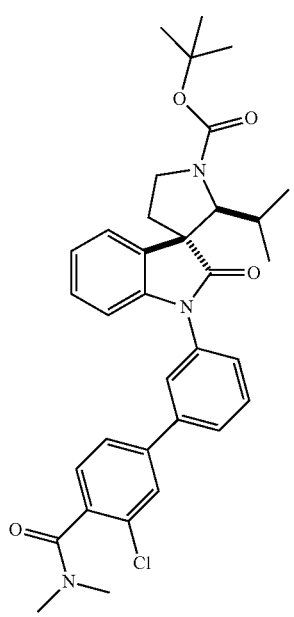
3b
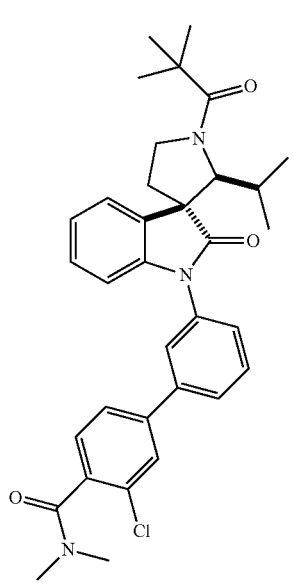

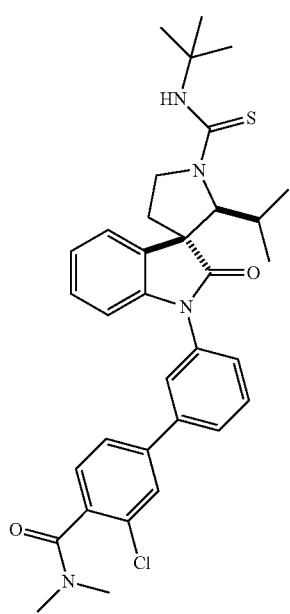
3c
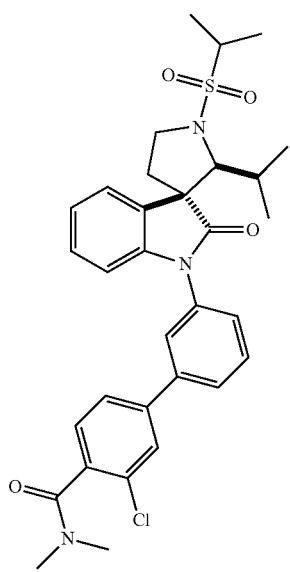
3d
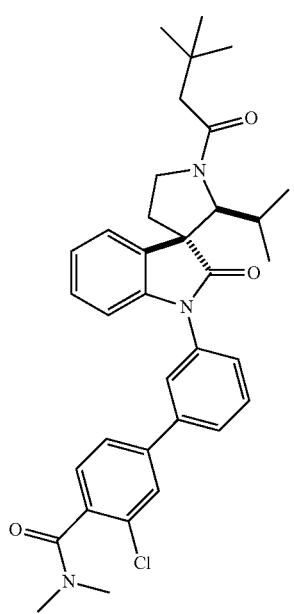
3e
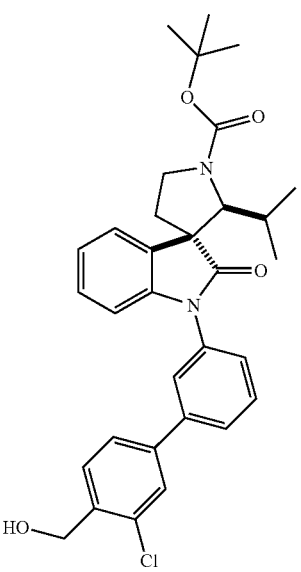
3f

4a

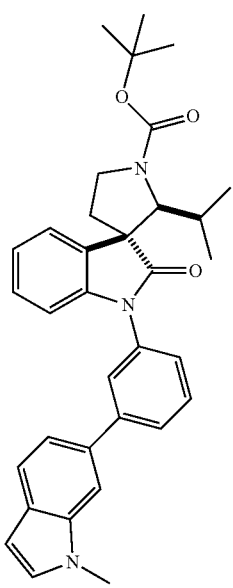

4b

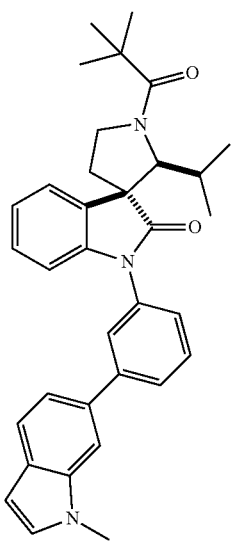

4c

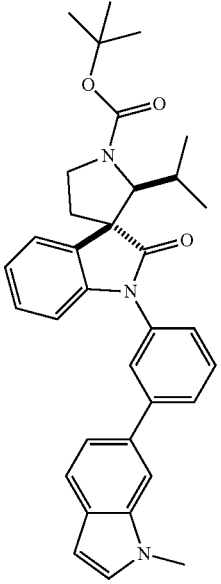

In a second aspect of the present disclosure, the present disclosure provides a pharmaceutical composition including the aforementioned compound.

According to an embodiment of the present disclosure, the pharmaceutical composition may further have at least one of the following additional technical features.

According to an embodiment of the present disclosure, the pharmaceutical composition further includes a pharmaceutically acceptable carrier, excipient, diluent, adjuvant, vehicle, or any combinations thereof.

According to an embodiment of the present disclosure, the pharmaceutical composition further includes an additional therapeutic agent. In some embodiments, the additional therapeutic agent is a medicament for treatment of hyperlipidemia, fatty liver, obesity, diabetes, metabolic syndrome, or a combination thereof. In other embodiments, the additional therapeutic agent is a medicament for treatment of glioblastoma, atherosclerosis, dyslipidemia, metabolic syndrome, Parkinson's disease, Alzheimer's disease, multiple sclerosis, atopic dermatitis, rheumatoid arthritis, or osteoporosis, or a combination thereof.

According to an embodiment of the present disclosure, the medicament for the treatment of hyperlipidemia, fatty liver, obesity, diabetes or metabolic syndrome is atorvastatin, gemfibrozil, acipimox, Eicosapentaenoic acid, metformin, glimepiride, repaglinide, empagliflozin, or any combination thereof.

According to an embodiment of the present disclosure, the medicament for the treatment of glioblastoma, atherosclerosis, dyslipidemia, metabolic syndrome, Parkinson's disease, Alzheimer's disease, multiple sclerosis, atopic dermatitis, rheumatoid arthritis, or osteoporosis is temozolomide, fotemustine, statin, fibrate, trihexyphenidyl, aspirin, non-steroidal anti-inflammatory medicament, or any combination thereof. In some embodiments, the statin is lovastatin or simvastatin; the fibrate is clofibrate, lifibrate or bezafibrate; and the non-steroidal anti-inflammatory medicament is diclofenac, nabumetone, or meloxicam.

In a third aspect of the present disclosure, the present disclosure provides use of the above-mentioned compound or the above-mentioned pharmaceutical composition in manufacture of a medicament or kit for regulating liver X receptors, for use in scientific researches. According to an embodiment of the present disclosure, the medicament or kit is used to inversely activate liver X receptors or used to activate liver X receptors.

In a fourth aspect of the present disclosure, the present disclosure provides use of the above-mentioned compound or the above-mentioned pharmaceutical composition in manufacture of a medicament. The medicament is used for treatment or prevention of hyperlipidemia, fatty liver, obesity, diabetes or metabolic syndrome, or for targeting at tumor energy metabolism; or the medicament is used for treatment or prevention of glioblastoma, atherosclerosis, dyslipidemia, metabolic syndrome, Parkinson's disease, Alzheimer's disease, multiple sclerosis, atopic dermatitis, rheumatoid arthritis, osteoporosis drugs or a combination thereof.

DESCRIPTION OF EMBODIMENTS

Figure 1:
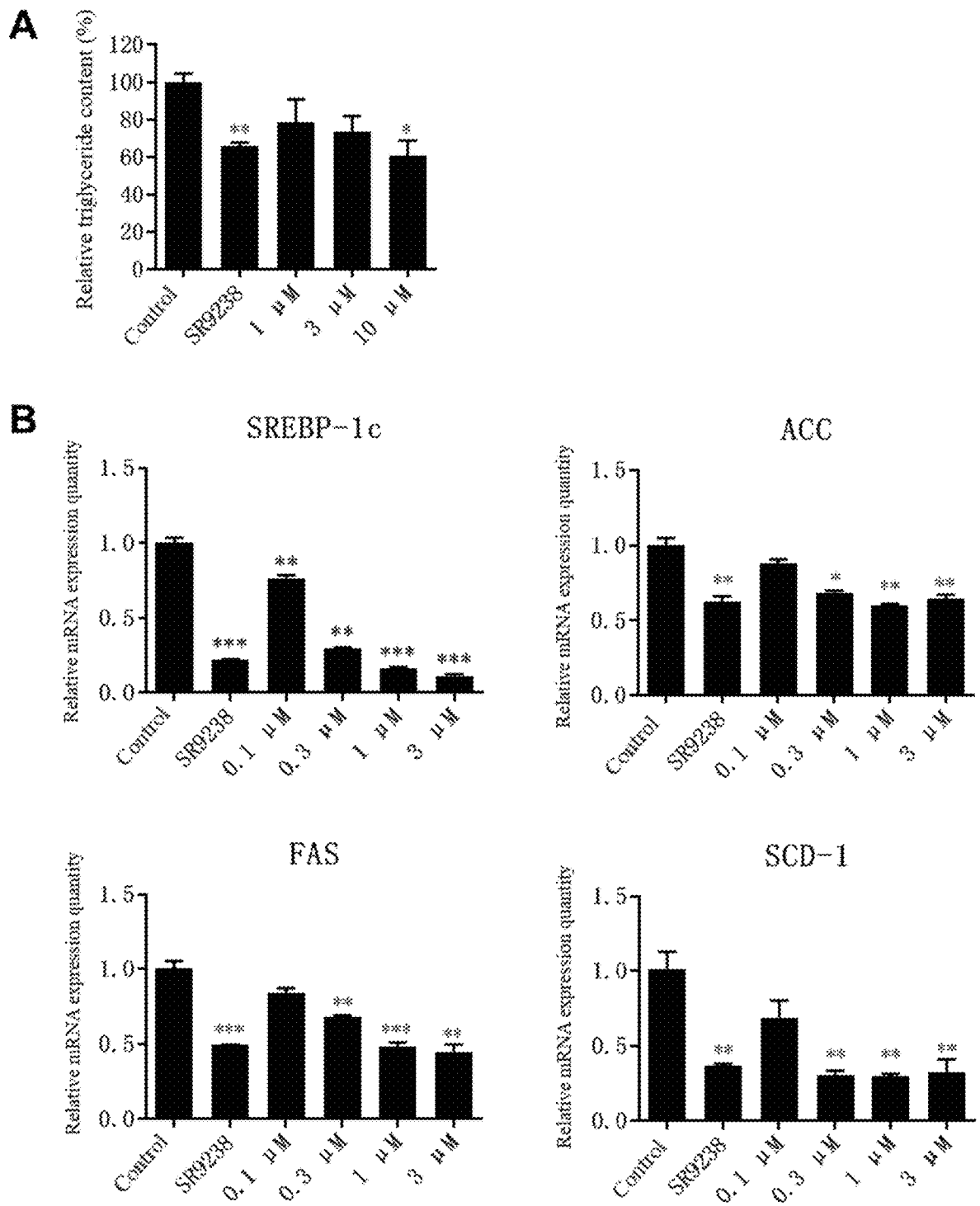
FIG. 1 is a schematic diagram illustrating a lipid-lowering activity of Compound 2a-1 according to an embodiment of the present disclosure in HepG2 cells and a mechanism thereof.

Embodiments of the present disclosure are described in detail below, and examples of the embodiments are shown in the accompanying drawings. The embodiments described below with reference to the accompanying drawings are illustrative, which aims to explain the present disclosure, but should not be interpreted as limiting the present disclosure.

The term "include" or "comprise" is an open-ended expression, i.e., including the content specified in the present disclosure but not excluding the content in other aspects.

"Stereoisomers" refer to compounds that have the same chemical structure but differ in the spatial arrangement of atoms or moieties. Stereoisomers include enantiomers, diastereomers, conformational isomers (rotamers), geometric isomers (cis/trans isomers), atropisomers, etc.

"Chirality" refers to a molecule that cannot overlap with its mirror image. "Achirality" refers to a molecule that can overlap with its mirror image.

"Enantiomers" refer to two isomers of a compound that are each a mirror image of the other one but cannot overlap with each other.

"Diastereomers" refer to stereoisomers that have two or more chiral centers and molecules of which are not mirror images of each other. Diastereomers have different physical properties such as melting point, boiling point, spectral properties and reactivity. A mixture of diastereomers can be separated by high-resolution analytical operations, for example, electrophoresis, and chromatography such as HPLC.

The definitions and rules of stereochemistry used in the present disclosure generally follow "McGraw-Hill Dictionary of Chemical Terms (1984)", S. P. Parker, Ed., McGraw-Hill Book Company, New York; and "Stereochemistry of Organic Compounds", Eliel, E. and Wilen, S., John Wiley & Sons, Inc., New York, 1994.

Many organic compounds exist in optically active forms, i.e., they are capable of rotating a plane of plane-polarized light. When describing optically active compounds, the prefixes D and L, or R and S are used to denote the absolute configurations of the molecule with respect to one or more chiral centers. The prefixes d and l, or (+) and (−) are symbols used to specify a rotation of plane-polarized light caused by a compound, where (−) or l indicates that the compound is levorotatory, and the prefix (+) or d indicates that the compound is dextrorotatory. When specific stereoisomers are enantiomers, and a mixture of such isomers is called an enantiomeric mixture. A mixture of enantiomers in 50:50 is called a racemic mixture or a racemate, which may occur when there is no stereoselectivity or stereospecificity in a chemical reaction or process.

Any asymmetric atom (for example, carbon, etc.) of the compound of the present disclosure can be present in a racemate- or enantiomer-enriched form, for example, present in (R)-, (S)-, or (R, S)-configuration. In some embodiments, in terms of (R)- or (S)-configuration, each asymmetric atom has an enantiomeric excess of at least 50%, an enantiomeric excess of at least 60%, an enantiomeric excess of at least 70%, an enantiomeric excess of at least 80%, an enantiomeric excess of at least 90%, an enantiomeric excess of at least 95%, or an enantiomeric excess of at least 99%.

In accordance with the selection of starting materials and methods, the compounds of the present disclosure may be present as one of the possible isomers or a mixture thereof, such as a racemate and a mixture of diastereomers, depending on the number of asymmetric carbon atoms. The optically active (R)- or (S)-isomers can be prepared using chiral synthons or chiral reagents, or resolved using conventional techniques. If the compound contains a double bond, the substituent may be in the E or Z configuration; and if the compound contains disubstituted cycloalkyl, the substituent of the cycloalkyl may have a cis or trans configuration.

Any obtained mixture of stereoisomers can be separated into pure or substantially pure stereoisomers, enantiomers, diastereomers according to the differences in physical and chemical properties of components, for example, by chromatography and/or fractional crystallization process.

The racemate of the obtained end-product or intermediate can be resolved into optical enantiomers by methods known to those skilled in the art, for example, by separating the obtained diastereomeric salts. Racemic products can also be separated by chiral chromatography, such as high-performance liquid chromatography (HPLC) using chiral adsorbents. Particularly, the enantiomers can be prepared by asymmetric synthesis, for example, referring to "Enantiomers, Racemates and Resolutions", Jacques, et al., Wiley Interscience, New York, 1981; "Principles of Asymmetric Synthesis", $2^{nd}$ Ed. Robert E. Gawley, Jeffrey Aubé, Elsevier, Oxford, U K, 2012; "Stereochemistry of Carbon Compounds", Eliel, E. L., McGraw-Hill, N Y, 1962; "Tables of Resolving Agents and Optical Resolutions", p. 268, Wilen, S. H., E. L. Eliel, Ed., Univ. of Notre Dame Press, Notre Dame, in 1972; and "Chiral Separation Techniques: A Practical Approach", Subramanian, G. Ed., Wiley-VCH Verlag GmbH & Co. KGaA, Weinheim, Germany, 2007.

The term "tautomer" or "tautomeric form" refers to structural isomers that have different energies and can be interconverted by crossing a low energy barrier. If tautomerism is possible (for example, in solution), a chemical equilibrium of tautomers can be reached. For example, protontautomer (also known as prototropic tautomer) includes interconversion through proton migration, such as ketone-enol isomerization and imine-enamine isomerization. Valence tautomer includes interconversion through recombination of some bonding electrons. A specific example of ketone-enol tautomerization is interconversion of 2,4-pentanedione and 4-hydroxy-3-penten-2-one tautomeric isomers. Another example of tautomerism is phenol-ketone tautomerization. A specific example of phenol-ketone tautomerization is interconversion of 4-hydroxypyridine and pyridin-4(1H)-one tautomeric isomers. Unless otherwise indicated, all tautomeric forms of the compound of the present disclosure shall fall within the scope of the present disclosure.

In each part of the present specification, the substituents of the compounds disclosed in the present disclosure are disclosed according to the group types or ranges. In particular, the present disclosure includes each independent subcombination of respective members within these group types and ranges. For example, the term "$C_1$-$C_6$ alkyl" specifically refers to independently disclosed methyl, ethyl, $C_3$ alkyl, $C_4$ alkyl, $C_5$ alkyl, and $C_6$ alkyl.

In each part of the present disclosure, linking substituents are described. When the structure clearly requires a linking group, the Markush variables listed for the group should be understood as the linking group. For example, if the structure requires a linking group and the Markush group definition of the variable recites "alkyl" or "aryl", it should be understood that the "alkyl" or "aryl" respectively represents the linking alkylene group or arylene group.

As described in the present disclosure, the compounds of the present disclosure can be optionally substituted with one or more substituents, such as the compounds represented by the above general formulas, or particular examples, subclasses, and a type of compounds included in the present disclosure. It should be understood that the term "optionally substituted" and the term "substituted or unsubstituted" are interchangeably used. Generally speaking, the term "optionally", whether it precedes the term "substituted", means that one or more hydrogen atoms in a given structure may be substituted or unsubstituted by specific substituents. Unless otherwise indicated, an optionally substituted group may have a substituent substituted at each substitutable position of the group. When more than one position in the given structural formula can be substituted by one or more substituents selected from specific groups, the substituents substituted at the respective positions can be the same or different from each other.

The term "alkyl" used in the present disclosure includes linear or branched saturated monovalent hydrocarbyl group of 1-20 carbon atoms, where the alkyl can be independently and optionally substituted with one or more substituents described in the present disclosure. In some embodiments, the alkyl group contains 1-10 carbon atoms; in some other embodiments, the alkyl group contains 1-8 carbon atoms; in some other embodiments, the alkyl group contains 1-6 carbon atoms; in some other embodiments, the alkyl group contains 1~4 carbon atoms; in some other embodiments, the alkyl group contains 1-3 carbon atoms; and in some other embodiments, the alkyl group contains 2-6 carbon atoms. Further examples of the alkyl group include, but are not limited to, methyl (Me, —$CH_3$), ethyl (Et, —$CH_2CH_3$), n-propyl (n-Pr, —$CH_2CH_2CH_3$), isopropyl (i-Pr, —$CH(CH_3)_2$), n-butyl (n-Bu, —$CH_2CH_2CH_2CH_3$), 2-methylpropyl or isobutyl (i-Bu, —$CH_2CH(CH_3)_2$), 1-methylpropyl or sec-butyl (s-Bu, —$CH(CH_3)CH_2CH_3$), tert-butyl (t-Bu, —$C(CH_3)_3$), n-pentyl (—$CH_2CH_2CH_2CH_2CH_3$), 2-pentyl (—$CH(CH_3)CH_2CH_2CH_3$), 3-pentyl(-$CH(CH_2CH_3)_2$), 2-methyl-2-butyl(-$C(CH_3)_2CH_2CH_3$), 3-methyl-2-butyl(-$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), n-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$), n-heptyl, n-octyl, etc. The term "alkane group" and its prefix "alkane" used herein both include straight and branched saturated carbon chains.

The term "halogenated alkyl" refers to that alkyl may be substituted with one or more identical or different halogen atoms, which are F, Cl, Br, or I. Herein, the alkyl group has the meaning as described in the present disclosure, and examples thereof include, but are not limited to, trifluoromethyl, 1-chloroethyl, difluoromethyl, 2-fluoroethyl, 3,3,3-trifluoropropyl, etc.

The term "hydroxyl-substituted alkyl" refers to that alkyl may be substituted with one or more hydroxyl groups. Herein, the alkyl group has the meaning as described in the present disclosure, and examples thereof include, but are not limited to, hydroxymethyl, 1-hydroxyethyl, dihydroxymethyl, 2-hydroxyethyl, 3,3,3-trihydroxypropyl, etc.

The term "amino" refers to —$NH_2$.

The term "alkoxy" used in the present disclosure involves alkyl, as defined in the present disclosure, connected to a main carbon chain through an oxygen atom. Such examples include, but are not limited to, methoxyl, ethoxy, propoxy, and the like.

The term "cycloalkyl" refers to a monovalent or multivalent saturated monocyclic, bicyclic or tricyclic ring system containing 3-12 carbon atoms. The bicyclic or tricyclic ring system may include fused rings, bridged rings, and spiro rings. In an embodiment, cycloalkyl contains 3-10 carbon atoms; in another embodiment, cycloalkyl contains 3-8 carbon atoms; in another embodiment, cycloalkyl contains 3-6 carbon atoms. Examples of cycloalkyl include, but are not limited to, cyclopropyl, cyclobutyl, cyclopentyl, cyclohexyl, and the like. The cycloalkyl group is optionally substituted with one or more substituents described in the present disclosure.

The term "aryl" refers to a monocyclic, bicyclic and tricyclic carbon ring system containing 6-14 ring atoms, or 6-12 ring atoms, or 6-10 ring atoms, at least one ring of which is aromatic. The aryl group is usually, but not necessarily, connected to the core moiety through the aromatic ring of the aryl group. The term "aryl" can be used interchangeably with the term "aromatic ring". Examples of the aryl may include phenyl, naphthyl, and anthracyl. The aryl group is optionally substituted with one or more substituents described in the present disclosure.

The term "heteroaromatic ring" refers to a monocyclic, bicyclic and tricyclic ring system containing 5-12 ring atoms, or 5-10 ring atoms, or 5-6 ring atoms, at least one ring of which is aromatic and at least one ring of which contains one or more heteroatoms. The heteroaromatic ring is usually, but not necessarily, connected to the core moiety through the aromatic ring of the heteroaromatic ring. The term "heteroaryl" can be used interchangeably with the term "heteroaromatic ring", "aromatic heterocyclic ring", or "heteroaromatic compound". The heteroaryl group is optionally substituted with one or more substituents described in the present disclosure. In an embodiment, the heteroaryl group, consisting of 5 to 10 atoms, contains 1, 2, 3, or 4 heteroatoms independently selected from O, S, or N.

Examples of the heteroaryl include, but are not limited to, 2-furyl, 3-furyl, N-imidazolyl, 2-imidazolyl, 4-imidazolyl, 5-imidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (such as 3-pyridazinyl), 2-thiazolyl, 4-thiazolyl, 5-thiazolyl, tetrazolyl (such as 5-tetrazolyl), triazolyl (such as 2-triazolyl and 5-triazolyl), 2-thienyl, 3-thienyl, pyrazolyl (such as 2-pyrazolyl), isothiazolyl, 1,2,3-oxadiazolyl, 1,2,5-oxadiazolyl, 1,2,4-oxadiazolyl, 1,2,3-triazolyl, 1,2,3-thiodiazolyl, 1,3,4-thiodiazolyl, 1,2,5-thiodiazolyl, pyrazinyl, 1,3,5-triazinyl. Examples of heteroaryl further include, but not limited to, the following bicyclic rings: benzimidazolyl, benzofuranyl, benzothienyl, indolyl (such as 2-indolyl), purinyl, quinolinyl (such as 2-quinolinyl, 3-quinolinyl, 4-quinolinyl), isoquinolinyl (such as 1-isoquinolinyl, 3-isoquinolinyl or 4-isoquinolinyl), imidazo[1,2-a]pyridinyl, pyrazolo[1,5-a]pyridyl, pyrazolo[1,5-a]pyrimidinyl, imidazo[1,2-b]pyridazinyl, [1,2,4]triazolo[4,3-b]pyridazinyl, [1,2,4]triazolo[1,5-a]pyrimidinyl, [1,2,4]triazolo[1,5-a]pyridyl, etc.

As described in the present disclosure, a ring system with a substituent R' connected to a core ring of the ring system through one bond represents that the substituent R' can be substituted at any substitutable or any suitable position on the ring. For example, formula a represents that any substitutable position on the B' ring can be substituted with R', e.g., shown in formula b, formula c and formula d.

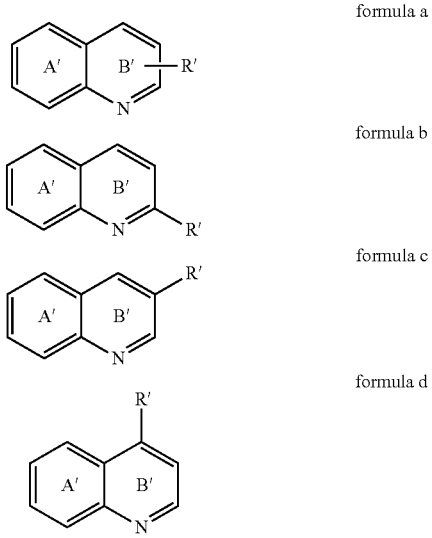

In addition, it should be noted that, unless explicitly stated otherwise, the expressions used throughout the present disclosure such as "each of . . . and . . . is independently", " . . . and . . . are each independently" and " . . . and . . . are respectively independently" are interchangeable and should be understood in a broad sense. They mean that in different groups, the specific options expressed by the same symbols do not affect each other; or in the same group, the specific options expressed by the same symbols do not affect each other. For example, in Formula (I), among m1 ($R^4$)s, the specific options of $R^4$ can be identical or different; for instance, in Formula (I), the specific options of respective $R^4$, $R^5$ or $R^6$ can be identical or different, and the substituents represented by $R^4$, $R^5$ and $R^6$ may be identical or different.

The term "pharmaceutically acceptable" refers to molecular entities and compositions that are physiologically tolerable when administered to humans and generally do not produce allergies or similar inappropriate reactions, such as gastrointestinal discomfort, dizziness, and the like. Preferably, the term "pharmaceutically acceptable" as used herein refers to those approved by a federal regulatory agency or a national government or recorded in the US Pharmacopoeia or other generally recognized pharmacopoeia for use in animals, more particularly in humans.

The term "carrier" refers to a diluent, adjuvant, excipient or matrix that is administered together with the compound. These pharmaceutical carriers can be sterile liquids such as water and oils, including those derived from petroleum, animals, plants, or synthetic sources, such as peanut oil, soybean oil, mineral oil, sesame oil, and the like. Water, aqueous saline solution, aqueous dextrose, and glycerite are preferably used as carriers, especially for injectable solutions. Suitable carriers of medicaments are described in "Remington's Pharmaceutical Sciences", by E. W. Martin.

The "hydrate" of the present disclosure refers to the compound or its salt provided by the present disclosure with chemical or non-chemical equivalent water bonded thereto by non-covalent intermolecular force, i.e., an associated complex formed when the solvent molecule is water.

The "solvate" of the present disclosure refers to an associated complex formed by one or more solvent molecules and the compound of the present disclosure. The solvents for forming the solvate include, but are not limited to, water, isopropanol, ethanol, methanol, dimethyl sulfoxide, ethyl acetate, acetic acid, and aminoethanol.

The "ester" in the present disclosure refers to esters that are formed by the compounds represented by Formula (I) to Formula (IV) containing hydroxyl and can be hydrolyzed in vivo. Such esters are, for example, pharmaceutically acceptable esters that are hydrolyzable in the human or animal body to produce alcohols. The in vivo hydrolyzable esters of the compounds represented by Formula (I) to Formula (IV) containing hydroxyl include, but are not limited to, phosphate group, acetyloxymethoxyl, 2,2-dimethyl acetyloxymethoxyl, alkanoyl, benzoyl, benzylacetyl, alkoxycarbonyl, dialkylcarbamoyl, and N-(dialkylaminoethyl)-N-alkylcarbamoyl, etc.

The "nitrogen oxide" of the present disclosure means that, when the compound contains several amine functional groups, one or more nitrogen atoms can be oxidized to form N-oxide. Specific examples of N-oxides are N-oxides of tertiary amines or N-oxides of the nitrogen atom of nitrogen heterocycle. An oxidant such as hydrogen peroxide or peracid (such as peroxycarboxylic acid) can be used to process a corresponding amine to form N-oxide (see Advanced Organic Chemistry, Wiley Interscience, 4th edition, Jerry March, pages). In particular, N-oxides can be prepared by the method by L. W. Deady (Syn. Comm. 1977, 7, 509-514), in which, for example, the amine compound reacts with m-chloroperoxybenzoic acid (MCPBA) in an inert solvent such as dichloromethane.

The term "prodrug" used in the present disclosure indicates a compound that is converted into a compound represented by formula (I) in vivo. Such conversion is affected by a prodrug hydrolysis in blood or an enzymatic conversion into a parent structure in blood or tissues. The prodrug compounds of the present disclosure may be esters. In the present disclosure, the esters serving as prodrugs include phenyl esters, aliphatic ($C_{1-24}$) esters, acyloxymethyl esters, carbonate esters, carbamate esters and amino acid esters. For example, a compound in the present disclosure contains hydroxyl, which can be acylated to obtain a compound in the form of a prodrug. Other forms of the prodrug include phosphate esters, for example, the phosphate ester compounds obtained by phosphorylation of the hydroxyl group on the parent structure. For a full discussion of prodrugs, please refer to the following literatures: T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, J. Rautio et al., Prodrugs: Design and Clinical Applications, *Nature Review Drug Discovery,* 2008, 7, 255-270, and S. J. Hecker et al., Prodrugs of Phosphates and Phosphonates, *Journal of Medicinal Chemistry,* 2008, 51, 2328-2345.

All tautomeric forms of the compounds of the present disclosure are included in the scope of the present disclosure, unless otherwise indicated.

In addition, the structural formulas of the compounds described in the present disclosure include enriched isotopes of one or more different atoms, unless otherwise indicated. The present disclosure includes isotopically-labeled compounds, which are equivalent to the compounds represented by formula (I) to formula (II), but one or more atoms thereof are replaced by atoms with atomic mass or mass number different from the common atomic mass or mass number in nature. Examples of isotopes that can be introduced in the compounds of the present disclosure include isotopes of hydrogen, carbon, nitrogen, oxygen, phosphorus, sulfur, fluorine, and chlorine, such as $^2$H, $^3$H, $^{13}$C, $^{11}$C, $^{14}$C, $^{14}$C, $^{15}$N, $^{18}$O, $^{17}$O, $^{31}$P, $^{32}$P, $^{35}$S, $^{18}$F and, $^{36}$Cl. The compounds of the present disclosure containing the above isotopes and/or other isotopes of other atoms, prodrugs thereof, and pharmaceutically acceptable salts of the compounds or the prodrugs all fall within the scope of the present disclosure. The isotopically-labeled compounds of formula (I) to formula (II) of the present disclosure and their prodrugs can generally be prepared in this way: when performing the following procedures and/or the processes disclosed in the examples and preparation examples, the non-isotopically labeled reagents are replaced by the isotopically-labeled reagents that are easily available.

"Metabolite" refers to a product obtained by metabolizing a specific compound or its salt in vivo. The metabolite of one compound can be identified by techniques well known in the art, and its activity can be characterized by assays as described in the present disclosure. Such a product may be obtained through oxidation, reduction, hydrolysis, amidation, deamidation, esterification, degreasing, or enzyme cleavage of the administered compound, or the like. Accordingly, the present disclosure includes the metabolites of the compound, including metabolites produced by fully contacting the compound of the present disclosure with a mammal for a period of time.

Various pharmaceutically acceptable salt forms of the compounds of the present disclosure are useful. The term "pharmaceutically acceptable salts" refers to the salt forms that are apparent to pharmaceutical chemists, that is, they are substantially non-toxic and can provide the desired pharmacokinetic properties, palatability, absorption, distribution, metabolism or excretion. Other factors, which are more practical in terms of properties and are also important in terms of selection, include: the cost of raw materials, ease of crystallization, yield, stability, hygroscopicity, and fluidity of the resulting crude drugs. In brief, the pharmaceutical composition can be prepared from an active component and a pharmaceutically acceptable carrier.

As used herein, a "pharmaceutically acceptable salt" refers to an organic or inorganic salt of the compound of the present disclosure. The pharmaceutically acceptable salts are well known in the art, as described in the literature: S. M. Berge et al., describe pharmaceutically acceptable salts in detail in J. Pharmaceutical Sciences, 66: 1-19, 1977. Salts formed by pharmaceutically acceptable non-toxic acids include, but are not limited to, inorganic acid salts formed by reacting with amino groups, including hydrochloride, hydrobromide, phosphate, sulfate, perchlorate, nitrate, etc; and organic acid salts such as acetate, propionate, glycollate, oxalate, maleate, malonate, succinate, fumarate, tartrate, citrate, benzoate, mandelate, methanesulfonate, ethanesulfonate, tosylate, sulfosalicylate, etc., or the salts obtained through other methods such as ion exchange described in book literatures.

Other pharmaceutically acceptable salts include adipate, malate, 2-hydroxypropionic acid, alginate, ascorbate, aspartate, benzenesulfonate, benzoate, bisulfate, borate, butyrate, camphorate, camphorsulfonate, cyclopentylpropionate, digluconate, dodecyl sulfate, esilate, formate, fumarate, gluceptate, glycerophosphate, gluconate, hemisulphate, enanthate, caproate, hydriodate, 2-hydroxy-ethanesulfonate, lactobionic acid salt, lactate, laurate, lauryl sulfate, malate, malonate, methanesulfonate, 2-naphthalenesulfonate, nicotinate, nitrate, oleate, palmitate, pamoate, pectate, persulfate, 3-phenylpropionate, picrate, pivalate, propionate, stearate, thiocyanate, p-toluene sulfonate, undecanoate, valerate, etc. Salts obtained from suitable bases include salts of alkali metal, alkaline earth metal, ammonium, and $N^+(C_{1-4} \text{alkyl})_4$.

The present disclosure also contemplates quaternary ammonium salts formed by any compound with a group containing N. Water-soluble or oil-soluble or dispersed products can be obtained by quaternization. The salts of alkali metal or alkaline earth metal include sodium salts, lithium salts, potassium salts, calcium salts, magnesium salts, iron salts, zinc salts, copper salts, manganese salts, aluminum salts, etc. The pharmaceutically acceptable salts further include suitable and non-toxic ammoniums, quaternary ammonium salts and amine cations formed by counterions, such as halides, hydroxides, carboxylates, hydrosulfates, phosphates, nitrates, $C_{1-8}$ sulfonates and aromatic sulfonates. The ammonium salts, such as but not limited to N, N'-dibenzylethylenediamine, chloroprocaine, choline, ammonia, diethanolamine and other hydroxyalkylamines, ethylenediamine, N-methyl glucosamine, procaine, N-benzylphenethylamine, 1-p-chlorobenzyl-2-pyrrolidine-1'-ylmethyl-benzimidazole, diethylamine and other alkylamines, piperazine, and tris(hydroxymethyl)aminomethane; alkaline earth metal salts, such as but not limited to barium, calcium and magnesium; transition metal salts, for example, including, but not limited to zinc.

In this specification, the structure shall prevail if the chemical name is different from the chemical structure.

Unless otherwise specified, the abbreviations of any amino acids and other compounds used in the present disclosure are the commonly used and recognized abbreviations, or refer to IUPAC-IUB Commission on Biochemical Nomenclature (see Biochem. 1972, 11: 942-944).

A first aspect of the present disclosure provides a new compound having a significant regulatory activity for liver X receptors.

A second aspect of the present disclosure provides a new compound that has significant therapeutic effects on hyperlipidemia, fatty liver, obesity, diabetes, and metabolic syndrome, and can target at tumor energy metabolism.

A third aspect of the present disclosure provides a method for preparing the liver X receptor regulator.

A fourth aspect of the present disclosure provides use of the compound in treatment of hyperlipidemia, fatty liver, obesity, diabetes, or metabolic syndrome and in targeting at tumor energy metabolism.

The present disclosure provides a method for preparing the 2'-isopropyl-spiro (3,3'-pyrrolidine oxindole) liver X receptor regulator. The method includes the following steps: dissolving tryptamine and isobutyraldehyde in dichloromethane and performing a Pictet-Spengler reaction in an acidic environment to obtain an intermediate 1a; dissolving the intermediate 1a in tetrahydrofuran for rearrangement under the presence of N-bromosuccinimide, so as to obtain an intermediate 1b; dissolving the intermediate 1b in dichloromethane, and adding triethylamine to react with di-tert-butyl decarbonate, so as to obtain an intermediate 1c; dissolving the intermediate 1c in toluene, and adding cuprous iodide, N,N-dimethylethylenediamine, and potassium carbonate to react with m-chloroiodobenzene to obtain an intermediate 1d; dissolving the intermediate 1d in 2,4-dioxane, and adding bis(dibenzylideneacetone) palladium, bis(pinacolato)diboron, and potassium acetate to react in a nitrogen atmosphere, so as to obtain an intermediate 1e; performing a Suzuki coupling reaction with the intermediate 1e and a bromo-substituted R1 fragment to obtain an intermediate 1f; removing protecting groups from the intermediate 1f under an acidic condition, and reacting with an acid anhydride and acyl chloride containing R2 to obtain the 2'-isopropyl-spiro (3,3'-pyrrolidine oxindole) liver X receptor regulator.

The compound provided by the present disclosure has a significant regulatory activity for the liver X receptor and lipid-lowering activity, and thus it can be used as a lead compound for treatment of hyperlipidemia, fatty liver, obesity, diabetes, and metabolic syndrome and for targeting at tumor energy metabolism.

Further, by using a reporter gene method on HEK293T cells, liver X receptor regulators are screened from the compounds provided by the present disclosure. The lipid-lowering activities of the compounds in hepatocytes and adipocytes are tested on HepG2 cells and 3T3-L1 cells. It was found that compound 2a-1 has the best regulatory activity for the liver X receptor and lipid-lowering activity, and the lipid-lowering mechanism thereof has been investigated. The results indicate that this compound exerts the lipid-lowering effect by down-regulating liver X receptor downstream genes SREBP-1c, ACC, FAS, SCD-1. At the same time, compound 2a-1 also has lipid-lowering activity in a mice hyperlipidemia model induced by Triton WR-1339.

Compared with the prior art, the present disclosure has the following beneficial effects:

The compounds provided by the present disclosure require raw materials that are easily available, can be easily prepared, and have the significant regulatory activity for liver X receptor and lipid-lowering activity. The 2'-isopropyl-spiro (3,3'-pyrrolidine oxindole) liver X receptor regulator exerts the lipid-lowering effect by down-regulating the liver X receptor downstream genes SREBP-1c, ACC, FAS, and SCD-1. Accordingly, the compounds of the present disclosure have great application prospects in the preparation of drugs for prevention and treatment of hyperlipidemia, fatty liver, obesity, diabetes, metabolic syndrome, and tumors.

The present application is further described below in conjunction with specific embodiments and drawings, which should not be understood as limitations of the present disclosure. Without departing from the spirit and essence of the present disclosure, simple modifications or substitutions made to the methods, steps or conditions of the present disclosure shall fall within the scope of the present disclosure; unless otherwise specified, the technical means used in the embodiments are those well-known and conventional for those skilled in the art.

Example 1: Synthesis of Compounds

Using tryptamine as the starting material, a 2'-isopropyl-spiro (3,3'-pyrrolidine oxindole) compound is obtained through six or seven steps of reaction. The reaction scheme is as follows:

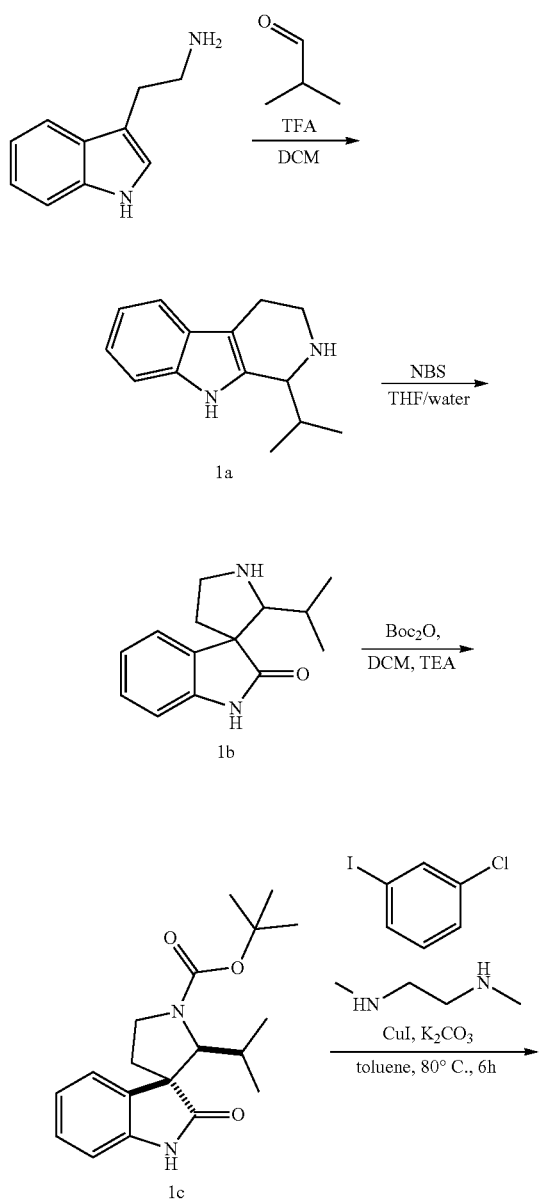

-continued

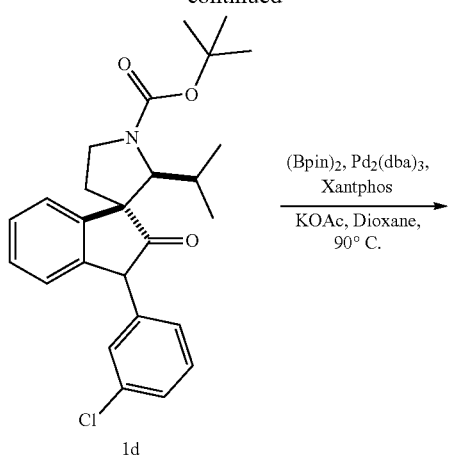

1d

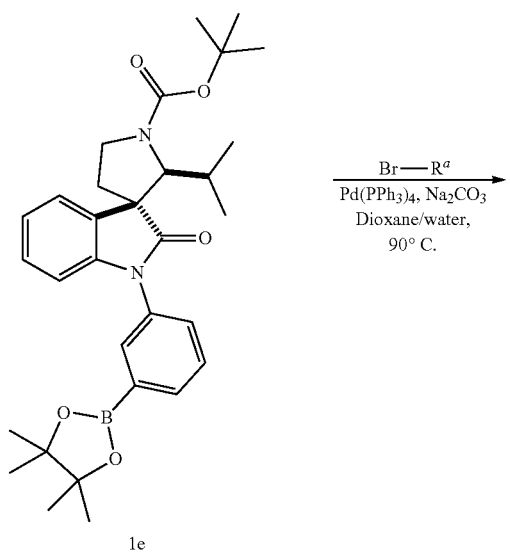

1e

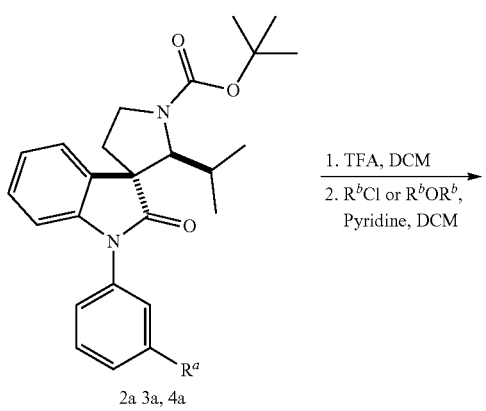

2a 3a, 4a

-continued

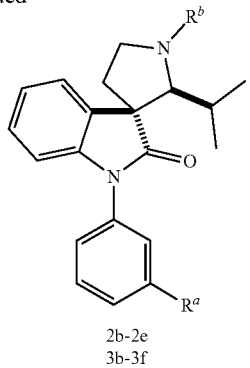

2b-2e
3b-3f
4b-4c

Specific steps are described as below.

1. Tryptamine (20 mmol) was dissolved in 50 mL of dichloromethane, isobutyraldehyde (20 mmol, 1 eq.) was added, then trifluoroacetic acid (40 mmol, 2 eq.) was slowly added, and the mixture was stirred overnight for reaction. Then, the reaction solution was added with petroleum ether and filtrated to obtain a white solid, i.e., an intermediate 1a.

2. The intermediate 1a (18 mmol) was dissolved in tetrahydrofuran/water solution, and N-bromosuccinimide (18 mmol, 1 eq.) was added at 0° C. and reacted for 4 hours. The reaction solution was extracted with ethyl acetate, washed with a saturated aqueous sodium of bicarbonate, dried over anhydrous sodium sulfate. Then, the solvent was removed by rotatory drying to obtain a crude intermediate 1b.

3. The intermediate 1b was dissolved in 50 mL of dichloromethane, triethylamine (20 mmol, 1.1 eq.) was added, and di-tert-butyl decarbonate was slowly added. After reacting for 2 hours, the reaction solution was diluted with dichloromethane, washed with a saturated aqueous solution of sodium bicarbonate, dried over anhydrous sodium sulfate. The solvent was removed by rotatory drying to obtain a crude intermediate 1c, which was then recrystallized by adding 30 mL of petroleum ether/ethyl acetate (v/v: 5/1) to obtain an intermediate 1c.

4. The intermediate 1c (15 mmol) was dissolved in toluene, and then potassium carbonate (15 mmol, 1 eq.), m-chloroiodobenzene (15 mmol, 1 eq.), N,N-dimethylethylenediamine (0.15 mmol, 0.01 eq.), and cuprous iodide (0.75 mmol, 0.05 eq.) were added. After reacting at 85° C. for 10 hours under nitrogen protection; the reaction solution was diluted with dichloromethane, washed with saturated ammonium chloride and sodium chloride aqueous solution, dried over anhydrous sodium sulfate. The solvent was then removed by rotatory drying to obtain a crude intermediate 1d, which was recrystallized by adding 30 mL of petroleum ether/ethyl acetate (v/v: 5/1) to obtain an intermediate 1d.

5. The intermediate 1d (10 mmol) was dissolved in 2,4-dioxane, and then potassium acetate (10 mmol, 1 eq.), bis(pinacolato)diboron (11 mmol, 1.1 eq.), bis(dibenzylideneacetone)palladium (0.5 mmol, 0.05 eq.), 4,5-bisdiphenylphosphine-9,9-dimethylxanthene (0.5 mmol, 0.05 eq.) were added. After reacting at 85° C. for 10 hours under nitrogen protection, the reaction solution was washed with saturated ammonium chloride and sodium chloride aqueous solution, and dried over anhydrous sodium sulfate. The solvent was removed by rotatory drying to obtain a crude intermediate 1e, which was purified through silica gel column chromatography to obtain a pure product.

6. The intermediate 1e (8 mmol) was dissolved in 2,4-dioxane, and then sodium carbonate (9.6 mmol, 1.2 eq.), a bromo-substituted W derivative (9.6 mmol, 1.2 eq.), and [1,1'-bis(diphenylphosphino)ferrocene]palladium dichloride (0.4 mmol, 0.05 eq.) were added. After reacting at 85° C. for 10 hours under nitrogen protection, the reaction solution was diluted with dichloromethane, washed with saturated ammonium chloride and sodium chloride aqueous solution, and dried over anhydrous sodium sulfate. The solvent was removed by rotatory drying to obtain a crude product, which was purified by silica gel column chromatography to obtain compounds 2a, 3a, 4a.

7. Compound 2a, 3a, or 4a was dissolved in dichloromethane, and then trifluoroacetic acid (5 eq.) was added to react for 1 hour. The reaction solution was dried through rotatory drying under reduced pressure, and then a next reaction step was directly performed. The crude intermediate was dissolved in dichloromethane/pyridine (v/v: 5/1), and acid anhydride or acid chloride containing $R^b$ was added to react overnight. The reaction solution was diluted with dichloromethane, washed with saturated sodium bicarbonate and sodium chloride aqueous solution, and dried over anhydrous sodium sulfate. The solvent was removed by rotatory drying to obtain a crude product, which was purified through silica gel column chromatography to obtain the target compounds 2b to 2e, 3b to 3f, 4b to 4c.

The structure, appearance, and NMR spectrum data of the final products 1a to 4e are shown below.

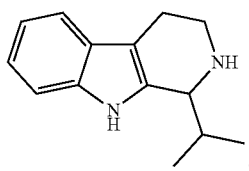

1a

Product 1a: white solid (92%). $^1$H NMR (400 MHz, Methanol-$d_4$) δ 7.48 (dd, J=7.95, 1.04 Hz, 1H), 7.37 (dt, J=8.21, 0.93 Hz, 1H), 7.16 (ddd, J=8.23, 7.04, 1.18 Hz, 1H), 7.06 (ddd, J=8.01, 7.05, 1.01 Hz, 1H), 4.67 (dd, J=4.02, 2.06 Hz, 1H), 3.75 (ddd, J=12.51, 5.50, 3.28 Hz, 1H), 3.45 (ddd, J=12.70, 9.70, 5.71 Hz, 1H), 3.18-3.00 (m, 2H), 2.64 (pd, J=7.10, 4.00 Hz, 1H), 1.25 (d, J=7.06 Hz, 3H), 0.97 (d, J=7.07 Hz, 3H). m/z (ESI-MS): 215.3 [M+H]$^+$.

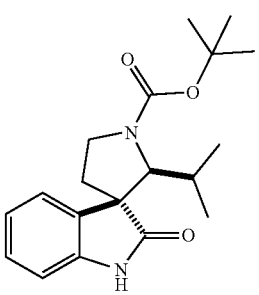

1c

Product 1c: white solid (81%). $^1$H NMR (400 MHz, Methanol-$d_4$) δ 9.45 (s, 1H), 7.24-7.18 (m, 1H), 7.15 (td, J=7.73, 1.16 Hz, 1H), 6.93 (td, J=7.61, 1.05 Hz, 1H), 6.86 (d, J=7.72 Hz, 1H), 4.00 (dt, J=11.02, 7.85 Hz, 1H), 3.91 (d, J=6.05 Hz, 1H), 3.43 (ddd, J=11.13, 7.42, 5.83 Hz, 1H), 2.20-2.10 (m, 2H), 2.00-1.86 (m, 1H), 1.42 (s, 9H), 0.94 (d, J=6.78 Hz, 3H), 0.62 (d, J=6.68 Hz, 3H). m/z (ESI-MS): 231.2[M+H]$^+$

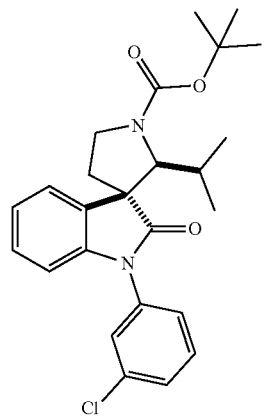

1d

Product 1d: white solid (58%). $^1$H NMR (400 MHz, Chloroform-d) δ 7.37-7.32 (m, 2H), 7.32-7.28 (m, 1H), 7.23 (m, 2H), 7.14 (td, J=7.74, 1.16 Hz, 1H), 7.00 (t, J=7.53 Hz, 1H), 6.75 (d, J=7.86 Hz, 1H), 3.98 (m, 2H), 3.46 (dt, J=11.18, 6.74 Hz, 1H), 2.21 (dd, J=8.41, 5.45 Hz, 2H), 2.00 (h, J=6.66 Hz, 1H), 1.39 (s, 9H), 0.94 (d, J=6.78 Hz, 3H), 0.63 (d, J=6.68 Hz, 3H). m/z (ESI-MS): 441.3[M+H]$^+$

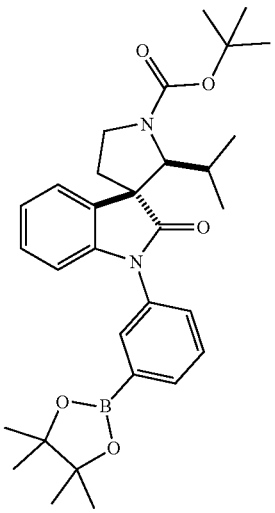

1e

Product 1e: white solid (63%). $^1$H NMR (400 MHz, Chloroform-d) δ 7.76 (d, J=7.22 Hz, 1H), 7.72 (d, J=2.00 Hz, 1H), 7.44 (t, J=7.56 Hz, 1H), 7.38 (d, J=8.44 Hz, 1H), 7.30 (d, J=7.42 Hz, 1H), 7.13 (t, J=7.71 Hz, 1H), 6.99 (t, J=7.50 Hz, 1H), 6.69 (d, J=7.88 Hz, 1H), 4.08-3.95 (m, 2H), 3.48 (dt, J=11.24, 6.71 Hz, 1H), 2.23 (m, 2H), 2.02 (q, J=6.66 Hz, 1H), 1.40 (s, 9H), 1.26 (s, 12H), 0.96 (d, J=6.81 Hz, 3H), 0.66 (d, J=6.65 Hz, 3H).

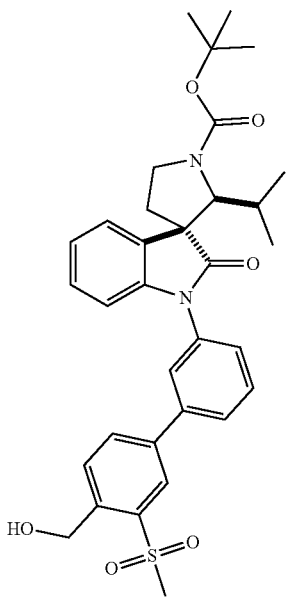
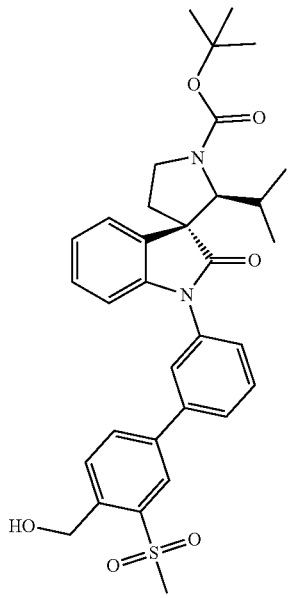
Product 2a: white solid (58%). $^1$H NMR (400 MHz, Chloroform-d) δ 8.14 (d, J=1.94 Hz, 1H), 7.74 (dd, J=7.92, 1.96 Hz, 1H), 7.59 (d, J=7.97 Hz, 1H), 7.57-7.47 (m, 3H), 7.34 (t, J=6.53 Hz, 2H), 7.16 (t, J=7.72 Hz, 1H), 7.02 (t, J=7.53 Hz, 1H), 6.77 (d, J=7.92 Hz, 1H), 4.90 (d, J=6.03 Hz, 2H), 4.11-3.86 (m, 2H), 3.63 (t, J=6.34 Hz, 1H), 3.48 (dt, J=11.17, 6.69 Hz, 1H), 3.09 (s, 3H), 2.39-2.20 (m, 2H), 2.04 (q, J=6.62 Hz, 1H), 1.37 (s, 10H), 0.97 (d, J=6.78 Hz, 3H), 0.68 (d, J=6.67 Hz, 3H). $^{13}$C NMR (101 MHz, CDCl$_3$) δ 177.63, 155.20, 142.50, 139.39, 139.36, 138.68, 137.77, 134.10, 131.45, 130.71, 129.36, 127.49, 127.35, 127.15, 125.75, 125.43, 124.33, 124.30, 121.89, 108.43, 78.74, 66.99, 61.10, 55.24, 44.82, 43.96, 34.42, 29.76, 27.43, 20.74.17.91. ESI-HRMS [M+H]$^+$ m/z=591.2520, calcd for C$_{33}$H$_{38}$N$_2$O$_6$S, 591.2523.
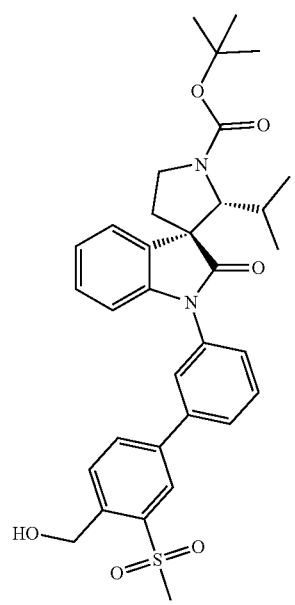
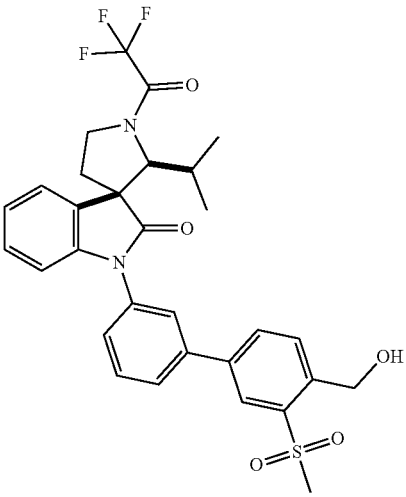
Product 2b: white solid (70%). $^1$H NMR (500 MHz, Chloroform-d) δ 8.17 (d, J=3.11 Hz, 1H), 7.78 (d, J=6.34 Hz, 1H), 7.58 (m, 4H), 7.36 (d, J=7.56 Hz, 2H), 7.25-7.20

(m, 1H), 7.08 (d, J=6.54 Hz, 1H), 6.81 (d, J=7.07 Hz, 1H), 4.91 (d, J=7.16 Hz, 1H), 4.42 (t, J=4.50 Hz, 1H), 4.23 (q, J=9.36 Hz, 1H), 3.88-3.79 (m, 1H), 3.63 (t, J=5.63 Hz, 1H), 3.13 (d, J=3.15 Hz, 3H), 3.12-3.05 (m, 2H), 2.49 (dd, J=8.73, 3.47 Hz, 1H), 2.44 (dd, J=8.65, 4.13 Hz, 1H), 2.18 (q, J=7.37, 6.89 Hz, 1H), 0.99 (d, J=5.84 Hz, 3H), 0.75 (d, J=6.63 Hz, 3H). $^{13}$C NMR (126 MHz, Chloroform-d) δ 178.00, 157.75 (q), 143.80, 140.77, 140.49, 139.41, 139.13, 134.78, 132.68, 132.19, 130.51, 129.18, 128.49, 127.08, 126.71, 126.51, 125.41, 125.31, 123.19, 116.55 (q), 109.85, 68.44, 62.65, 54.50, 45.17, 45.04, 34.38, 30.35, 22.02, 18.58. ESI-HRMS [M+H]$^+$ m/z=587.1819, calcd for $C_{30}H_{29}F_3N_2O_5S$, 587.1822.

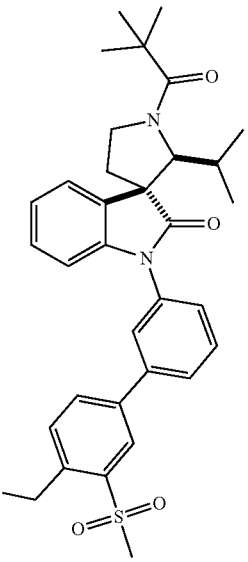

2d

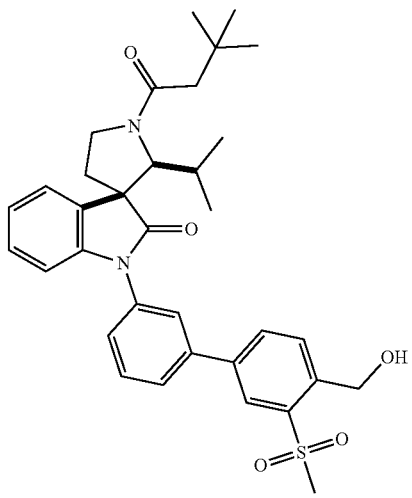

2c

Product 2d: white solid (78%). $^1$H NMR (500 MHz, Chloroform-d) δ 8.15 (d, J=1.84 Hz, 1H), 7.75 (dd, J=7.86, 1.86 Hz, 1H), 7.58 (d, J=7.87 Hz, 1H), 7.57-7.49 (m, 3H), 7.35 (dd, J=7.61, 3.15 Hz, 2H), 7.23-7.14 (m, 1H), 7.04 (t, J=7.54 Hz, 1H), 6.76 (d, J=7.86 Hz, 1H), 4.90 (s, 2H), 4.56 (d, J=6.76 Hz, 1H), 4.23 (dt, J=10.47, 7.49 Hz, 1H), 3.77 (dt, J=10.44, 7.05 Hz, 1H), 3.40 (s, 1H), 3.12 (s, 3H), 2.40 (t, J=7.20 Hz, 2H), 2.07 (h, J=6.79 Hz, 1H), 1.26 (s, 9H), 0.90 (d, J=6.81 Hz, 3H), 0.65 (d, J=6.59 Hz, 3H). $^{13}$C NMR (126 MHz, CDCl$_3$) δ 177.67, 177.11, 142.79, 139.65, 139.39, 138.47, 137.93, 134.13, 131.59, 131.00, 129.40, 127.57, 127.32, 127.12, 125.86, 125.70, 124.54, 124.14, 121.74, 108.46, 67.08, 61.42, 53.33, 45.32, 44.07, 38.44, 34.42, 29.30, 27.00, 20.88, 17.68. ESI-HRMS [M+H]$^+$ m/z=575.2541, calcd for $C_{33}H_{38}N_2O_5S$, 575.2574.

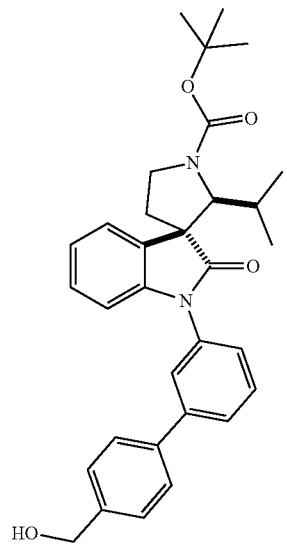

2e

Product 2c: white solid (84%). $^1$H NMR (400 MHz, Chloroform-d) δ 8.15 (d, J=1.84 Hz, 1H), 7.75 (dd, J=7.90, 1.90 Hz, 1H), 7.56 (dd, J=13.86, 5.20 Hz, 5H), 7.39-7.27 (m, 2H), 7.24-7.11 (m, 1H), 7.04 (t, J=7.55 Hz, 1H), 6.78 (d, J=7.87 Hz, 1H), 4.91 (s, 2H), 4.42 (d, J=6.03 Hz, 1H), 4.03 (q, J=8.81 Hz, 1H), 3.66 (td, J=9.58, 3.28 Hz, 1H), 3.39 (d, J=12.98 Hz, 1H), 3.12 (s, 3H), 2.45 (dt, J=13.30, 8.69 Hz, 1H), 2.40-2.32 (m, 1H), 2.19 (d, J=14.27 Hz, 1H), 2.08 (q, J=6.63 Hz, 1H), 1.02 (s, 8H), 0.97 (d, J=6.88 Hz, 3H), 0.72 (d, J=6.63 Hz, 3H). $^{13}$C NMR (101 MHz, CDCl$_3$) δ 177.50, 171.70, 142.77, 139.65, 139.37, 138.51, 137.97, 134.06, 131.58, 131.09, 131.00, 129.34, 127.66, 127.58, 127.46, 127.32, 126.64, 125.81, 125.54, 124.45, 124.25, 121.82, 108.49, 65.36, 61.42, 53.97, 45.75, 45.43, 44.09, 33.34, 30.36, 29.68, 29.09, 21.35, 18.06. ESI-HRMS [M+H]$^+$ m/z=589.2734, calcd for $C_{34}H_{40}N_2O_5S$, 589.2731.

Product 2e: white solid (63%). $^1$H NMR (400 MHz, Chloroform-d) δ 7.67-7.55 (m, 5H), 7.47 (d, J=7.79 Hz, 2H), 7.43 (d, J=7.61 Hz, 1H), 7.40 (dd, J=7.46, 1.73 Hz, 1H), 7.26

(d, J=7.84 Hz, 1H), 7.12 (t, J=7.54 Hz, 1H), 6.92 (d, J=7.91 Hz, 1H), 4.77 (s, 2H), 4.13 (d, J=7.06 Hz, 2H), 3.60 (dt, J=12.04, 6.78 Hz, 1H), 2.38 (td, J=19.24, 16.22, 9.53 Hz, 2H), 2.14 (h, J=6.62 Hz, 1H), 1.51 (d, J=1.52 Hz, 9H), 1.07 (dd, J=6.92, 1.48 Hz, 3H), 0.76 (d, J=6.64 Hz, 3H). $^{13}$C NMR (101 MHz, CDCl$_3$) δ 178.51, 156.16, 143.79, 142.50, 140.49, 139.48, 134.89, 130.00, 128.79, 128.37, 127.48, 127.39, 126.71, 125.45, 125.24, 122.66, 109.52, 79.79, 64.99, 56.23, 46.06, 35.76, 30.80, 29.70, 28.48, 21.49, 19.00. ESI-HRMS [M+H]$^+$ m/z=513.2724, calcd for C$_{32}$H$_{36}$N$_2$O$_4$, 513.2748.

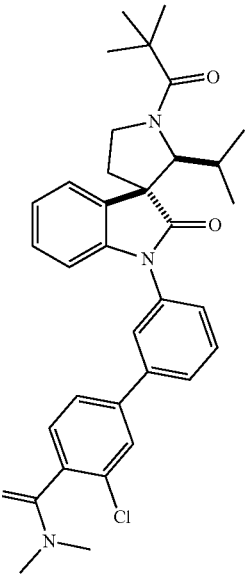

3a

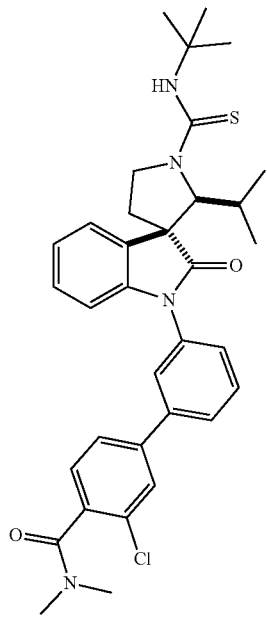

3b

Product 3b: white solid (77%). $^1$H NMR (500 MHz, Chloroform-d) δ 7.64-7.57 (m, 1H), 7.55 (d, J=1.59 Hz, 1H), 7.51 (t, J=6.62 Hz, 2H), 7.47 (dd, J=7.87, 1.60 Hz, 1H), 7.39 (td, J=7.72, 2.71 Hz, 1H), 7.34 (dd, J=7.02, 2.26 Hz, 2H), 7.30 (d, J=7.90 Hz, 1H), 7.22-7.15 (m, 1H), 7.04 (t, J=7.53 Hz, 1H), 4.57 (d, J=6.78 Hz, 1H), 4.23 (dt, J=10.47, 7.41 Hz, 1H), 3.77 (dt, J=10.45, 6.99 Hz, 1H), 3.09 (s, 3H), 2.85 (s, 3H), 2.38 (t, J=7.21 Hz, 2H), 2.07 (h, J=6.80 Hz, 1H), 1.28 (s, 9H), 0.91 (d, J=6.80 Hz, 3H), 0.64 (d, J=6.60 Hz, 3H). $^{13}$C NMR (126 MHz, CDCl$_3$) δ 177.57, 177.00, 167.22, 142.81, 141.25, 139.76, 134.38, 134.04, 129.27, 127.53, 127.51, 127.23, 127.21, 127.19, 125.76, 125.50, 125.11, 124.49, 124.13, 121.66, 108.43, 67.10, 53.33, 45.32, 38.44, 37.14, 34.45, 33.69, 29.30, 27.01, 20.82, 17.68. ESI-HRMS [M+H]$^+$ m/z=572.2659, calcd for C$_{34}$H$_{38}$ClN$_3$O$_3$, 572.2674.

3c

Product 3a: white solid (76%). $^1$H NMR (400 MHz, Chloroform-d) δ 7.62 (s, 1H), 7.61-7.56 (m, 3H), 7.54 (d, J=8.00 Hz, 1H), 7.41 (t, J=6.97 Hz, 2H), 7.36 (d, J=7.91 Hz, 1H), 7.24 (t, J=7.80 Hz, 1H), 7.09 (t, J=7.55 Hz, 1H), 6.87 (d, J=7.92 Hz, 1H), 4.09 (q, J=7.12 Hz, 2H), 3.56 (dt, J=12.24, 6.81 Hz, 1H), 3.14 (s, 3H), 2.90 (s, 3H), 2.40-2.26 (m, 2H), 2.10 (q, J=6.67 Hz, 1H), 1.47 (s, 9H), 1.04 (d, J=6.75 Hz, 3H), 0.74 (d, J=6.62 Hz, 3H). $^{13}$C NMR (101 MHz, CDCl$_3$) δ 178.51, 168.16, 156.11, 143.51, 142.24, 140.67, 135.45, 135.11, 130.86, 130.24, 128.55, 128.45, 128.27, 128.14, 126.63, 126.20, 126.07, 125.35, 125.30, 122.84, 109.41, 79.62, 74.81, 68.13, 60.33, 56.23, 45.92, 38.11, 34.68, 30.77, 28.47, 21.62. ESI-HRMS [M+H]$^+$ m/z=588.2617, calcd for C$_{34}$H$_{38}$ClN$_3$O$_4$, 588.2624.

Product 3c: white solid (49%). ¹H NMR (400 MHz, Chloroform-d) δ 7.64 (m, 3H), 7.58-7.53 (m, 1H), 7.45 (s, 1H), 7.40 (d, J=2.49 Hz, 1H), 7.38 (t, J=3.51 Hz, 1H), 7.29 (d, J=2.83 Hz, 1H), 7.28-7.23 (m, 1H), 7.12 (d, J=7.39 Hz, 1H), 6.91 (d, J=8.02 Hz, 1H), 4.80 (d, J=7.01 Hz, 1H), 4.33 (q, J=8.46 Hz, 1H), 3.41-3.37 (m, 1H), 3.75 (td, J=9.55, 3.82 Hz, 1H), 3.17 (s, 3H), 2.93 (s, 3H), 2.56-2.47 (m, 1H), 2.39-2.27 (m, 1H), 2.05 (brs, 3H), 1.58 (s, 6H), 0.83 (d, J=6.66 Hz, 3H), 0.60 (d, J=6.52 Hz, 3H). ¹³C NMR (101 MHz, CDCl₃) δ 179.80, 176.78, 167.20, 142.65, 141.58, 139.71, 134.45, 133.95, 131.22, 129.87, 129.23, 127.77, 127.26, 127.17, 126.61, 125.70, 125.06, 124.33, 124.03, 122.08, 108.53, 73.91, 68.21, 55.48, 54.79, 53.15, 47.12, 44.25, 40.02, 37.12, 33.69, 28.26. ESI-HRMS [M+H]⁺ m/z=604.2557, calcd for $C_{34}H_{39}ClN_4O_2S$, 604.2555.

34.72, 31.56, 28.36, 27.67, 22.09, 19.02. ESI-HRMS [M+H]⁺ m/z=594.2178, calcd for $C_{32}H_{36}ClN_3O_4S$, 594.2188.

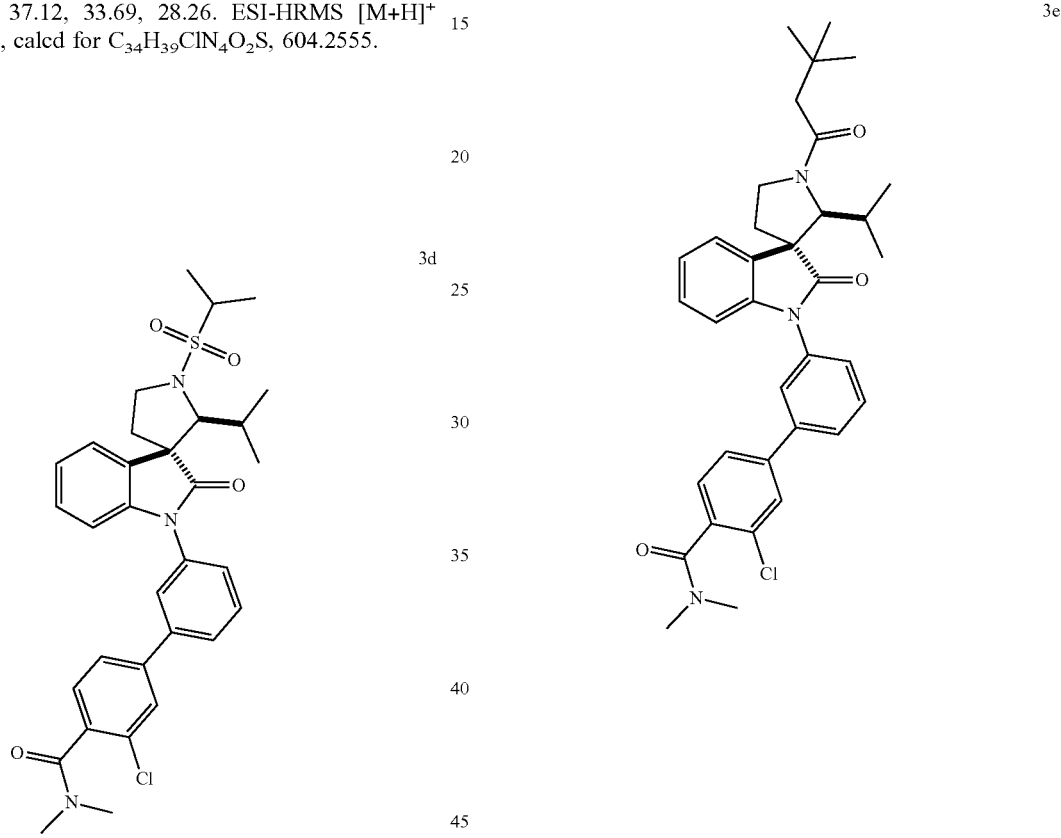

Product 3d: white solid (43%). ¹H NMR (400 MHz, Chloroform-d) δ 7.68-7.61 (m, 3H), 7.59 (d, J=2.13 Hz, 1H), 7.56 (dd, J=7.86, 1.63 Hz, 1H), 7.44 (t, J=7.62 Hz, 2H), 7.40 (d, J=7.92 Hz, 1H), 7.32 (t, J=7.75 Hz, 1H), 7.16 (t, J=7.51 Hz, 1H), 6.96 (d, J=7.92 Hz, 1H), 4.45 (dd, J=11.03, 8.60 Hz, 1H), 4.10 (d, J=8.34 Hz, 1H), 3.36 (td, J=11.63, 5.60 Hz, 1H), 3.18 (s, 3H), 2.94 (s, 3H), 2.47 (td, J=11.99, 8.65 Hz, 1H), 2.03-1.93 (m, 2H), 1.97 (d, J=7.21 Hz, 1H), 1.92 (s, 6H), 1.09 (d, J=6.70 Hz, 3H), 0.60 (d, J=6.76 Hz, 3H). ¹³C NMR (101 MHz, CDCl₃) δ 176.48, 168.18, 142.56, 142.21, 140.89, 135.56, 135.13, 130.94, 130.42, 130.37, 128.40, 128.32, 128.20, 126.90, 126.09, 125.97, 125.14, 125.06, 122.97, 109.84, 84.38, 75.11, 56.94, 40.96, 40.42, 38.14, Product 3e: white solid (75%). ¹H NMR (400 MHz, Chloroform-d) δ 7.62 (d, J=1.72 Hz, 1H), 7.58 (dq, J=4.12, 2.68, 1.96 Hz, 3H), 7.54 (dd, J=7.92, 1.74 Hz, 1H), 7.41 (ddd, J=7.02, 3.24, 1.68 Hz, 2H), 7.37 (d, J=7.92 Hz, 1H), 7.29-7.22 (m, 1H), 7.11 (td, J=7.58, 1.09 Hz, 1H), 6.87 (d, J=7.86 Hz, 1H), 4.48 (d, J=6.05 Hz, 1H), 4.10 (dt, J=10.05, 8.30 Hz, 1H), 3.72 (td, J=9.49, 3.36 Hz, 1H), 3.16 (s, 3H), 2.91 (s, 3H), 2.51 (dt, J=13.15, 8.72 Hz, 1H), 2.41-2.36 (m, 1H), 2.37 (d, J=14.32 Hz, 1H), 2.28 (d, J=14.28 Hz, 1H), 2.15 (h, J=6.88 Hz, 1H), 1.11 (s, 9H), 1.04 (d, J=6.83 Hz, 3H), 0.78 (d, J=6.65 Hz, 3H). ¹³C NMR (101 MHz, CDCl₃) δ 177.42, 171.59, 167.22, 142.78, 141.23, 139.73, 134.39, 133.93, 129.85, 129.21, 127.60, 127.23, 127.19, 126.69, 125.70, 125.31, 125.09, 124.40, 124.23, 121.74, 108.46, 65.33, 53.94, 45.72, 45.39, 37.13, 33.69, 33.32, 30.34, 29.68, 29.08, 21.31, 18.05. ESI-HRMS [M+H]⁺ m/z=586.2834, calcd for $C_{35}H_{40}ClN_3O_3$, 586.2831.

3f

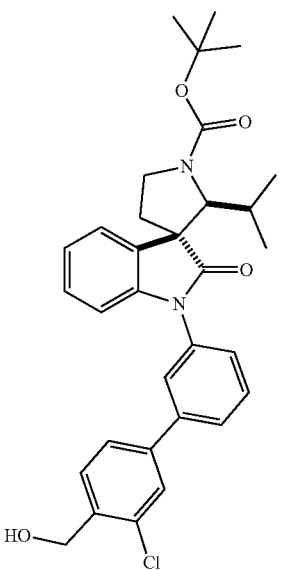

Product 3f: white solid (61%). $^1$H NMR (400 MHz, Chloroform-d) δ 7.58-7.49 (m, 4H), 7.48 (s, 1H), 7.44 (dd, J=8.00, 1.78 Hz, 1H), 7.33 (td, J=6.08, 3.36 Hz, 2H), 7.184 (t, J=6.85 Hz 1H), 7.03 (t, J=6.76 Hz 1H), 6.81 (d, J=7.92 Hz, 1H), 4.75 (s, 2H), 4.03 (d, J=6.58 Hz, 2H), 3.50 (dt, J=11.50, 7.22 Hz, 1H), 2.37-2.14 (m, 1H), 2.05 (dt, J=13.26, 6.87 Hz, 2H), 1.41 (d, J=3.89 Hz, 9H), 0.98 (d, J=6.77 Hz, 3H), 0.68 (d, J=6.63 Hz, 3H). $^{13}$C NMR (101 MHz, CDCl$_3$) δ 177.50, 155.15, 142.61, 140.09, 139.85, 136.58, 133.96, 132.09, 129.13, 128.04, 127.61, 127.39, 126.86, 125.62, 124.94, 124.75, 124.26, 124.20, 121.73, 108.43, 78.72, 61.51, 56.40, 49.84, 44.96, 34.60, 29.78, 27.45, 20.55, 17.95. ESI-HRMS [M+H]$^+$ m/z=545.2554, calcd for C$_{33}$H$_{37}$ClN$_2$O$_3$, 545.2565.

4a

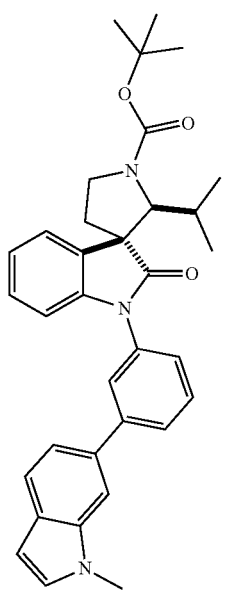

Product 4a: white solid (75%). $^1$H NMR (400 MHz, Chloroform-d) δ 7.73 (td, J=8.43, 7.83, 3.14 Hz, 3H), 7.62 (t, J=7.79 Hz, 1H), 7.57 (s, 1H), 7.45 (d, J=7.58 Hz, 1H), 7.43-7.40 (m, 1H), 7.38 (dd, J=7.85, 1.77 Hz, 1H), 7.32-7.19 (m, 1H), 7.18-7.05 (m, 2H), 6.95 (d, J=7.91 Hz, 1H), 6.54 (d, J=3.05 Hz, 1H), 4.17 (d, J=5.78 Hz, 2H), 3.87 (s, 3H), 3.62 (ddd, J=11.26, 7.78, 5.71 Hz, 1H), 2.39 (overlapped, 2H), 2.17 (q, J=6.66 Hz, 1H), 1.53 (s, 9H), 1.10 (d, J=6.76 Hz, 3H), 0.80 (d, J=6.67 Hz, 3H). $^{13}$C NMR (101 MHz, CDCl$_3$) δ 177.49, 155.15, 143.23, 142.95, 136.15, 133.72, 132.93, 128.84, 128.77, 127.73, 127.34, 127.14, 126.11, 124.51, 124.16, 123.70, 121.53, 120.12, 118.15, 108.59, 106.89, 99.83, 78.63, 67.16, 55.44, 45.04, 34.71, 31.91, 29.78, 27.47, 20.49, 17.98. ESI-HRMS [M+H]$^+$ m/z=536.2912, calcd for C$_{34}$H$_{37}$N$_3$O$_4$, 536.2908.

4b

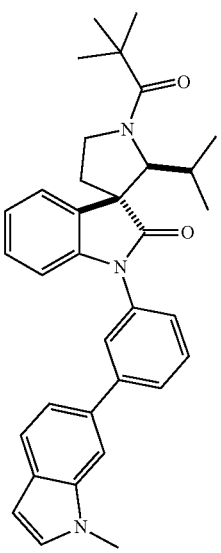

Product 4b: white solid (82%). $^1$H NMR (500 MHz, Chloroform-d) δ 7.63 (d, J=9.08 Hz, 2H), 7.59 (d, J=6.69 Hz, 1H), 7.50 (t, J=7.82 Hz, 1H), 7.46 (s, 1H), 7.34 (d, J=7.52 Hz, 1H), 7.30 (dd, J=8.31, 1.43 Hz, 1H), 7.25 (d, J=7.57 Hz, 1H), 7.16 (d, J=7.73 Hz, 1H), 7.06-6.96 (m, 2H), 6.81 (d, J=7.89 Hz, 1H), 6.43 (d, J=3.04 Hz, 1H), 4.59 (d, J=6.79 Hz, 1H), 4.25 (dt, J=10.33, 7.36 Hz, 1H), 3.78 (overlapped, 4H), 2.44-2.35 (m, 2H), 2.08 (h, J=6.83 Hz, 1H), 1.29 (s, 9H), 0.91 (d, J=6.83 Hz, 3H), 0.66 (d, J=6.61 Hz, 3H). $^{13}$C NMR (126 MHz, CDCl$_3$) δ 177.56, 161.42, 143.26, 136.14, 133.66, 132.95, 128.90, 128.75, 127.43, 127.33, 127.10, 126.25, 124.63, 124.00, 123.98, 121.39, 120.10, 118.17, 108.63, 106.97, 99.81, 67.17, 53.37, 45.41, 38.46, 34.60, 31.97, 29.33, 27.03, 20.76, 17.71. ESI-HRMS [M+H]$^+$ m/z=520.2945, calcd for C$_{34}$H$_{37}$N$_3$O$_2$, 520.2959.

4c

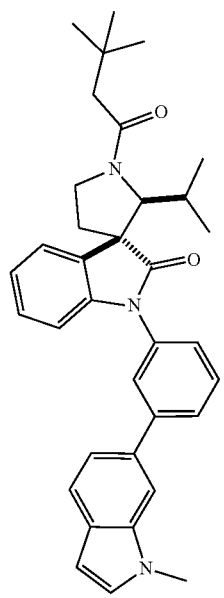

Product 4c: white solid (80%). $^1$H NMR (500 MHz, Chloroform-d) δ 7.66-7.60 (m, 2H), 7.59 (dd, J=4.48, 2.71 Hz, 1H), 7.50 (t, J=7.84 Hz, 1H), 7.47 (s, 1H), 7.33 (d, J=7.56 Hz, 1H), 7.30 (dd, J=8.26, 1.41 Hz, 1H), 7.25 (d, J=8.13 Hz, 1H), 7.17 (d, J=7.77 Hz, 1H), 7.06-6.92 (m, 2H), 6.82 (d, J=7.90 Hz, 1H), 6.43 (d, J=3.02 Hz, 1H), 4.44 (d, J=6.06 Hz, 1H), 3.78 (s, 3H), 3.67 (dd, J=9.61, 3.51 Hz, 1H), 3.63 (brs, 1H), 2.44 (dt, J=13.25, 8.66 Hz, 1H), 2.38-2.30 (m, 2H), 2.29 (d, J=14.34 Hz, 1H), 2.23 (d, J=14.31 Hz, 1H), 2.10 (h, J=6.75 Hz, 1H), 1.05 (s, 9H), 0.98 (d, J=6.79 Hz, 3H), 0.73 (d, J=6.67 Hz, 3H). $^{13}$C NMR (126 MHz, CDCl$_3$) δ 177.42, 170.14, 143.23, 136.14, 133.57, 132.91, 128.85, 128.76, 127.52, 127.11, 126.79, 126.20, 124.54, 124.11, 123.85, 121.47, 120.10, 118.16, 108.65, 106.96, 99.80, 65.36, 53.96, 45.74, 45.44, 33.45, 31.97, 30.34, 29.70, 21.28, 20.03, 18.07. ESI-HRMS [M+H]$^+$ m/z=534.3109, calcd for C$_{35}$H$_{39}$N$_3$O$_2$, 534.3115.

Example 2: Liver X Receptor Activity Test of the Compounds Obtained in Example 1

(1) Cell culture: human embryonic kidney cells (HEK293T cells) were cultured in DMEM (high glucose) medium containing 10% fetal bovine serum and 1% penicillin-streptomycin under conditions of 37° C. and 5% CO$_2$.

(2) Transfection: HEK293T cells were seeded in a 96-well plate with a cell density of 2×10$^4$ cells/well. After 24 hours, the cells were transfected according to instructions of Lipofectamine™ 3000 reagent. The specific steps of transfection were as follows:

① adding 15 μL of L3000 reagent to 500 μL of DMEM (high sugar) medium, and vortex oscillating for 2 seconds;

② mixing 6.5 μg of pGL3/(DR-4)-c-fos-FF-luc plasmid, 0.13 μg of pCMV/Renilla-luc plasmid, 1.3 μg of pSG5/hLXRα (or pSG5/hLXRβ plasmid), 1.3 μg of pSG5/hRXRα plasmid, and 19 μL of P3000 reagent in 500 μL of DMEM (high sugar) medium;

③ adding the plasmid mixture to a liposome mixture and standing by at room temperature for 20 minutes; and ④ adding 10 μL of liposome-DNA solution to each well of the 96-well plate, and gently shaking the 96-well plate to mix well.

(3) Drug intervention: after 5 hours of transfection, the compounds to be tested were added, and the plate was placed in an incubator to continue culturing for 20 hours.

(4) Detection: dual-luciferase reporter gene system was used for detection. The specific steps of detection were as follows:

① aspirating the original medium in the 96-well plate, adding cell lysate to the 96-well plate at 20 μL/well, and quickly shaking the plate at room temperature for 20 minutes;

② adding samples to a 384-well plate at 20 μL/well;

③ adding firefly luciferase substrate to each well at 10 μL/well, and measuring chemiluminescence after 7 seconds; and ④ adding Renilla luciferase substrate to the same sample well at 100 μL/well, and measuring chemiluminescence after 7 seconds.

Result processing: the results were analyzed using Renilla luciferase activity to correct the firefly luciferase activity. The liver X receptor inverse agonist activity of the compounds is shown in Table 1. By analyzing Table 1, it can be found that compounds 2a, 2a-1, 2a-2, 2b, 2c, 2d, etc. can inversely activate liver X receptors. Among them, compound 2a-1 has the best inverse agonist activity, and thus it was used for the study of lipid-lowering activity and mechanism. In addition, the liver X receptor agonist activities of the compounds are shown in Table 2. From Table 2, it can be seen that compounds 3a, 3b, and 3c can activate liver X receptors.

TABLE 1

Liver X receptor inverse agonist activity of the compounds

| | LXRα | | LXRβ | |
|---|---|---|---|---|
| Compound | IC$_{50}$ (μM)$^a$ | % Inverse agonist effect$^b$ | IC$_{50}$ (μM)$^a$ | % Inverse agonist effect$^b$ |
| SR9238 | 0.16 | 93 | 0.10 | 78 |
| 2a | 3.23 | 77 | 0.39 | 83 |
| 2a-1 | 2.25 | 81 | 0.36 | 85 |
| 2a-2 | 9.06 | 56 | 1.04 | 75 |
| 2b | 8.16 | 50 | 3.44 | 59 |
| 2c | 8.57 | 46 | 1.79 | 77 |
| 2e | NA | NA | 8.64 | 59 |
| 2d | 7.54 | 55 | 2.40 | 78 |
| 3d | 3.56 | 66 | 4.57 | 56 |
| 3e | NA | NA | NA | NA |
| 3f | NA | NA | 6.97 | 51 |
| 4a | NA | NA | NA | NA |
| 4b | NA | NA | NA | NA |
| 4c | NA | NA | 10.08 | 64 |

TABLE 2

Liver X receptor agonist activity of the compounds.

| | LXRα | | LXRβ | |
|---|---|---|---|---|
| Compound | EC$_{50}$ (μM)$^a$ | % Agonist effect$^b$ | EC$_{50}$ (μM)$^a$ | % Agonist effect$^b$ |
| GW3965 | 0.36 | 100 | 0.21 | 100 |
| 3a | 6.92 | 53 | NA | NA |
| 3b | 3.67 | 76 | 3.04 | 50 |
| 3c | 7.83 | 89 | 4.90 | 60 |

Example 3: Study on Lipid-Lowering Activity of Compound 2a-1 Obtained in Example 1 in HepG2 Cells and 3T3-L1 Cells (1) Cell culture: human liver cancer cells (HepG2 cells) and mouse pre-adipocytes (3T3L1 cells) were cultured in DMEM (high glucose) medium containing 10% fetal bovine serum and 1% penicillin-streptomycin under conditions of 37° C. and 5% $CO_2$.

(2) HepG2 cells were seeded in a 12-well plate, cultured with DMEM (low sugar) medium and starved for 12 hours. When the cells grow to a density of 70%, the medium was changed to DMEM (high sugar) medium and the compound was added to act for 24 hours.

(3) The steps of differentiation preadipocytes 3T3-L1 were as follows:

Cells were seeded in a 48-well plate, cultured in complete medium until the cells were completely in contact (day 0), and the medium was changed to a differentiation medium I (complete medium supplemented with 2 µg/mL of insulin, 100 ng/mL of dexamethasone, 0.5 mM of 3-isobutyl-1-methylxanthine, and 10 ng/mL of biotin) to culture for 3 days. The blank control group was still continued being cultured with the complete medium. On day 3, the medium was changed to a differentiation medium II (complete medium supplemented with 2 µg/mL of insulin) and culturing was continued for 3 days. On day 6, the cells were harvested for subsequent analysis.

(4) Triglyceride test: the treated cells were harvested, washed twice with icy PBS (0.2 M NaCl, 10 mM $Na_2HPO_4$, 3 mM KCl, 2 mM $KH_2PO_4$, pH 7.4), breaking the cells with ultrasonic waves, and detecting absorbance at 510 nm using the triglyceride detection kit (Nanjing Jiancheng Bioengineering Institute).

The detection results of the triglyceride content (FIG. 1) indicate that, at a concentration of 10 µM, the compound 2a-1 can significantly reduce the triglyceride accumulation in HepG2 cells induced by high glucose. In addition, the compound 2a-1 lowers the triglyceride level in 3T3-L1 cells in a concentration-dependent manner, with an $IC_{50}$ of 0.27±0.03 µM. The above results substantiate that the compound 2a-1 has significant lipid-lowering activity in HepG2 cells and 3T3-L1 cells.

Example 4: Study on Lipid-Lowering Activity of Compound 2a-1 Obtained in Example 1 in HepG2 Cells and 3T3-L1 Cells HepG2 cells were seeded in a 6-well plate with a cell density of $8 \times 10^5$ cells/well and incubated for 24 hours. The compounds to be tested were added and acted for 24 hours, and then the cells were harvested. The 3T3-L1 cells were harvested on day 6 of differentiation. The cells were washed twice with PBS, total RNA was extracted with RNAiso plus reagent, 1 µg of total RNA was reverse transcribed into cDNA using ReverTra Ace qPCR RT Master Mix, and PCR amplification was performed using SYBR Green Realtime PCR Master Mix.

Figure 2:
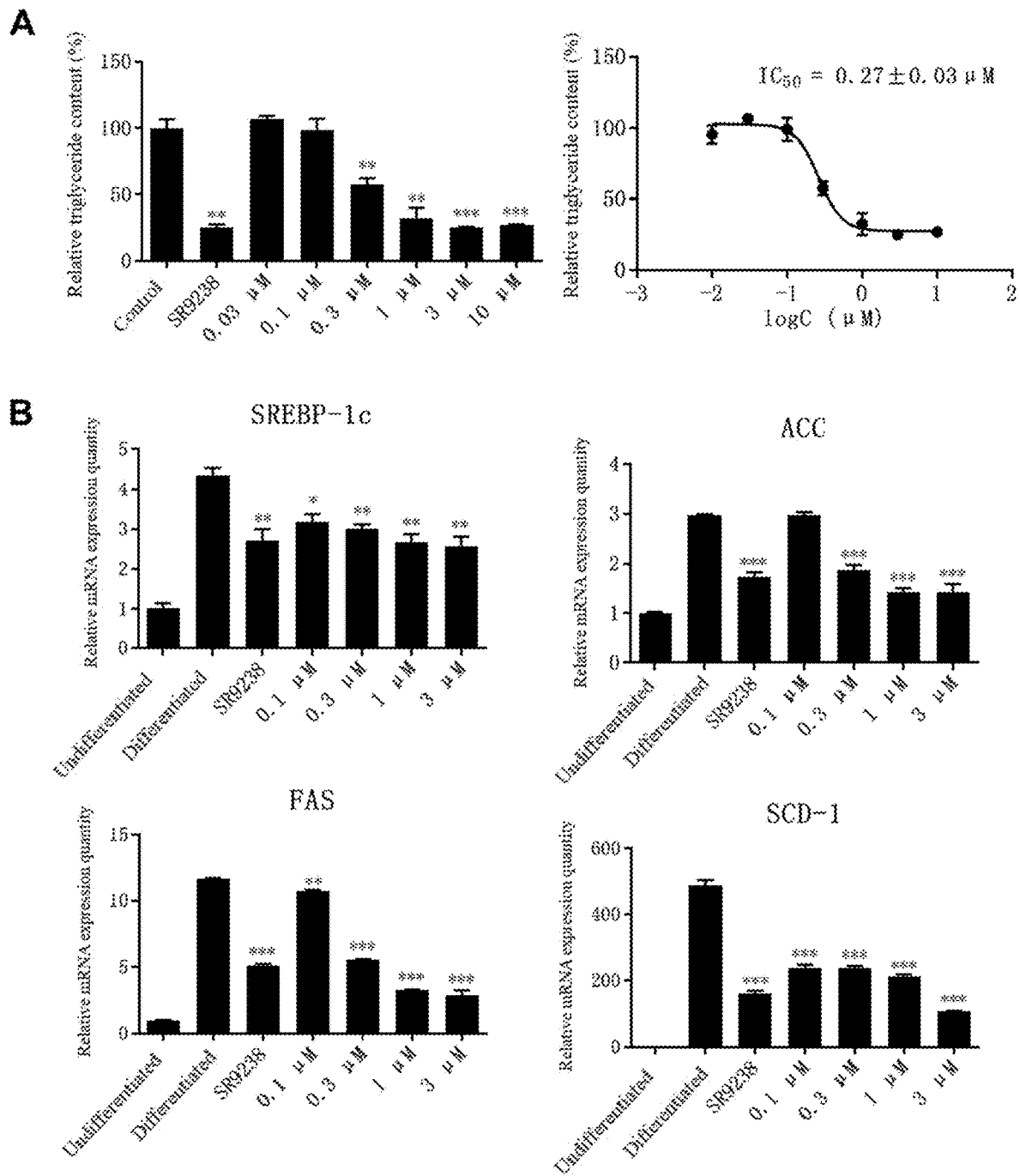
FIG. 2 is a schematic diagram illustrating a lipid-lowering activity of Compound 2a-1 according to an embodiment of the present disclosure in 3T3L1 cells and a mechanism thereof.

As shown in FIG. 2, in 3T3-L1 cells, the compound 2a-1 reduced the mRNA content of SREBP-1c, ACC, FAS and SCD-1 in a concentration-dependent manner. In HepG2 cells, the compound 2a-1 significantly reduced the mRNA content of these four genes. The above results prove that the compound 2a-1 can inhibit the expressions of SREBP-1c, ACC, FAS, and SCD-1 in 3T3-L1 cells and HepG2 cells, thereby inhibiting fat synthesis.

Example 5: Study on Lipid-Lowering Activity of Compound 2a-1 Obtained in Example 1 in Triton WR-1339-Induced Hyperlipidemia Mice 6-week-old SPF female C57BL/6J mice were purchased from the Experimental Animal Center of Sun Yat-sen University. The mice were randomly divided into 4 groups each including 6 mice, i.e., a normal control group, model a group, a fenofibrate group (100 mg/kg), and a B1 group (100 mg/kg), and intragastric administration was performed for 8 days. 24 hours before the last administration, the normal control group was intramuscularly injected with saline, and the remaining groups were injected with Triton WR-1339 (1500 mg/kg). One hour after the last administration, the eyeballs were removed to collect blood, the mice were executed by cervical dislocation, and the livers were collected. The plasma was allowed to stand for 1 hour, and the supernatant was collected by centrifugation at 4° C. and 3000 rpm. 100 mg of liver was weighed, added with methanol in 3 times the volume of the weighed liver, and homogenized thoroughly. Chloroform was then added in 6 times the volume and vortex oscillated. After centrifuging at 3000 rpm for 10 minutes, the lower chloroform layer was collected, and evaporated naturally overnight in a fume hood. 150 µL of 1% Triton ethanol was added and heated at 65° C. to be fully dissolved. Finally, triglycerides (TG), total cholesterol (TC), low-density lipoprotein cholesterol (LDL-C), and high-density lipoprotein cholesterol (HDL-C) in serum and liver samples were detected.

Figure 3:
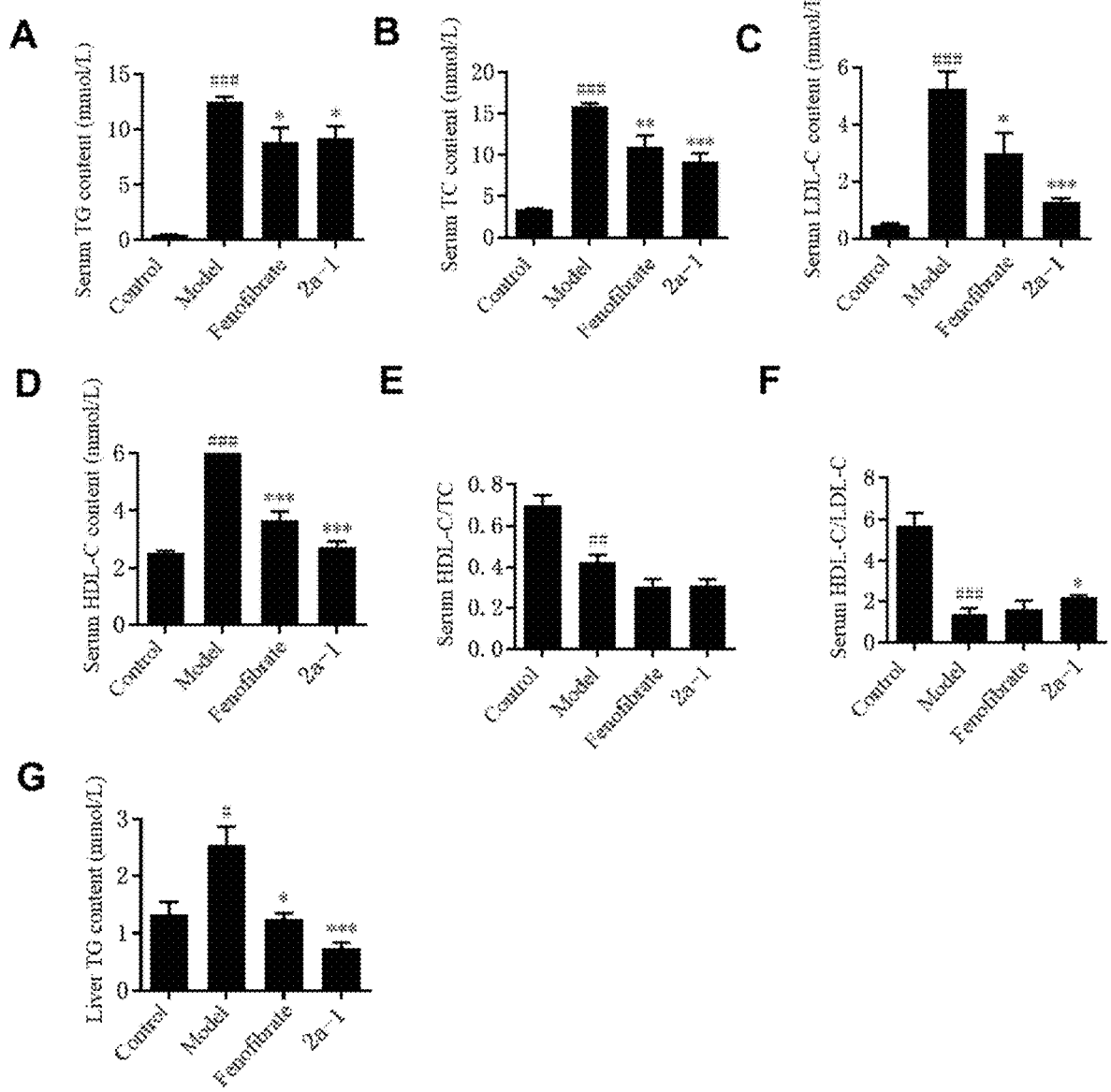
FIG. 3 illustrates a lipid-lowering activity of Compound 2a-1 according to an embodiment of the present disclosure in mice with hyperlipidemia induced by Triton WR-1339.

As illustrated in FIG. 3, the positive drug, fenofibrate and compound 2a-1, can significantly inhibit the increases in TG level, TC level, LDL-C level, and HDL-C level that are induced by Triton WR-1339. Neither fenofibrate nor compound 2a-1 had a significant effect on HDL-C/TC, but compound 2a-1 slightly increased HDL-C/LDL-C level. The above results indicate that the compound 2a-1 can significantly reduce the blood lipid levels in the Triton WR-1339-induced hyperlipidemia mice. At the same time, compound 2a-1 can reduce the triglyceride content in the livers of mice. There were no significant differences in liver cholesterol levels between the groups. The above results indicate that compound 2a-1 can significantly reduce the accumulation of triglycerides in the livers of Triton WR-1339-induced hyperlipidemia mice. In summary, compound 2a-1 also has significant lipid-lowering activity in mice.

CONCLUSION

The above experimental results indicate that the compound of the present disclosure has the significant inverse agonist activity for the liver X receptor, and can inhibit the expressions of target genes SREBP-1c, ACC, FAS and SCD-1 of liver X receptors to have lipid-lowering effect. Therefore, the compound of the present disclosure can be used as a lead compound for the treatment of hyperlipidemia, fatty liver, obesity, diabetes, and metabolic syndrome and for targeting tumor energy metabolism.

In the description of this specification, the description referring to the terms "an embodiment", "some embodiments", "an example", "specific examples", or "some examples" means that the specific features, structures, materials or characteristics described in conjunction with the embodiment or example are included in at least one embodiment or example of the present disclosure. In this specification, the schematic expression of the above terms does not necessarily refer to the same embodiment or example. Moreover, the described specific features, structures, materials, or characteristics may be combined in any one or more embodiments or examples in any suitable manner. In addition, without contradicting each other, different embodiments or examples and features of different embodiments or examples described in the specification can be combined by those skilled in the art.

Although the embodiments of the present disclosure have been shown and described above, it should be understood that the above-mentioned embodiments are illustrative and shall not be interpreted as limiting the present disclosure, and within the scope of the present disclosure, those skilled in the art can make changes, modifications, replacements and variations to the above embodiments.

What is claimed is:

1. A compound, being a compound represented by Formula (I); or being a stereoisomer, geometric isomer, tautomer, nitrogen oxide, hydrate, solvate, or pharmaceutically acceptable salt of the compound represented by Formula (I):

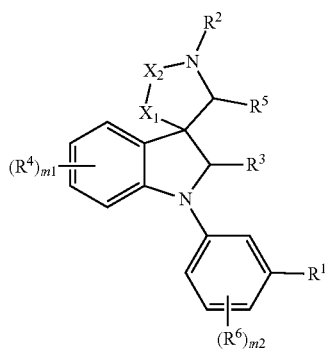

Formula (I)

wherein $X_1$ and $X_2$ are independently $C(R^{7a})_2$, O, S or $NR^8$;

wherein $R^1$ is H, D, F, Cl, Br, I, —CN, —NO$_2$, —OH, —NH$_2$, —COOH, $C_{1-6}$ alkyl, $C_{2-6}$ alkenyl, $C_{2-6}$ alkynyl, $C_{3-8}$ cycloalkyl, $C_{1-6}$ halogenated alkyl, $C_{1-6}$ hydroxyl-substituted alkyl, $C_{1-6}$ alkoxyl, $C_{1-6}$ halogenated alkoxyl, —C(=O)R$^{7b}$, —C(=O)OR$^{7b}$, —OC(=O)R$^{7b}$, —C(=O)NR$^{8a}$R$^{8b}$, —NR$^8$C(=O)R$^{7b}$, R$^{8a}$R$^{8b}$N—S(=O)$_2$—, —R$^8$N—S(=O)$_2$R$^{7b}$, R$^{7b}$S(=O)$_2$—, $C_{6-10}$ aryl, or heteroaryl consisting of 5-12 atoms, wherein one, two, three, four or five carbon atoms of the $C_{6-10}$ aryl or heteroaryl consisting of 5-12 atoms are independently and optionally substituted with $R^{10}$, wherein $R^{10}$ is each independently H, D, F, Cl, Br, I, —CN, —NO$_2$, —OH, —NH$_2$, —COOH, $C_{1-6}$ alkyl, $C_{2-6}$ alkenyl, $C_{2-6}$ alkynyl, $C_{3-8}$ cycloalkyl, $C_{1-6}$ halogenated alkyl, $C_{1-6}$ hydroxyl-substituted alkyl, $C_{1-6}$ alkoxyl, $C_{1-6}$ halogenated alkoxyl, —C(=O)R$^{7b}$, —C(=O)OR$^{7b}$, —OC(=O)R$^{7b}$, —C(=O)NR$^{8a}$R$^{8b}$, —NR$^8$C(=O)R$^{7b}$, R$^{8a}$R$^{8b}$N—S(=O)$_2$—, —R$^8$N—S(=O)$_2$R$^{7b}$, or R$^{7b}$S(=O)$_2$—;

wherein $R^2$ is —C(=O)R$^{7c}$, —C(=O)(C(R$^{7a}$)$_2$)$_{n1}$R$^{7c}$, —C(=O)OR$^{7c}$, —OC(=O)R$^{7c}$, —C(=O)NR$^{8a}$R$^{8b}$, —C(=S)NR$^{8a}$R$^{8b}$, —NR$^8$C(=O)R$^{7c}$, R$^{8a}$R$^{8b}$N—S(=O)$_2$—, —R$^8$N—S(=O)$_2$R$^{7c}$, or R$^{7c}$S(=O)$_2$—;

wherein $R^3$ is H, D, F, Cl, Br, I, —CN, —NO$_2$, —OH, —NH$_2$, —COOH, O, or $C_{1-6}$ alkyl;

wherein $R^4$, $R^5$, and $R^6$ are each independently H, D, F, Cl, Br, I, —CN, —NO$_2$, —OH, —NH$_2$, —COOH, or $C_{1-6}$ alkyl;

wherein $R^{7a}$, $R^{7b}$, $R^{7c}$, $R^8$, $R^{8a}$, and $R^{8b}$ are each independently H, D, F, Cl, Br, I, —CN, —NO$_2$, —OH, —NH$_2$, —COOH, $C_{1-6}$ alkyl, or $C_{1-6}$ halogenated alkyl; and wherein m1, m2, and n1 are independently 0, 1, 2, 3, or 4.

2. The compound according to claim 1, wherein $R^1$ is H, D, F, Cl, Br, I, —CN, —NO$_2$, —OH, —NH$_2$, —COOH, $C_{1-6}$ alkyl, $C_{2-4}$ alkenyl, $C_{2-4}$ alkynyl, $C_{3-6}$ cycloalkyl, $C_{1-4}$ halogenated alkyl, $C_{1-4}$ hydroxyl-substituted alkyl, $C_{1-4}$ alkoxyl, $C_{1-4}$ halogenated alkoxyl, —C(=O)R$^{7b}$, —C(=O)OR$^{7b}$, —OC(=O)R$^{7b}$, —C(=O)NR$^{8a}$R$^{8b}$, —NR$^8$C(=O)R$^{7b}$, R$^{8a}$R$^{8b}$N—S(=O)$_2$—, —R$^8$N—S(=O)$_2$R$^{7b}$, R$^{7b}$S(=O)$_2$—, $C_{6-10}$ aryl, or heteroaryl consisting of 5-10 atoms, wherein one, two, three, four or five carbon atoms of the $C_{6-10}$ aryl or heteroaryl consisting of 5-10 atoms are independently and optionally substituted with $R^{10}$, wherein $R^{10}$ is each independently H, D, F, Cl, Br, I, —CN, —NO$_2$, —OH, —NH$_2$, —COOH, $C_{1-4}$ alkyl, $C_{2-4}$ alkenyl, $C_{2-4}$ alkynyl, $C_{3-6}$ cycloalkyl, $C_{1-4}$ halogenated alkyl, $C_{1-4}$ hydroxyl-substituted alkyl, $C_{1-4}$ alkoxyl, $C_{1-4}$ halogenated alkoxyl, —C(=O)R$^{7b}$, —C(=O)OR$^{7b}$, —OC(=O)R$^{7b}$, —C(=O)NR$^{8a}$R$^{8b}$, —NR$^8$C(=O)R$^{7b}$, R$^{8a}$R$^{8b}$N—S(=O)$_2$—, —R$^8$N—S(=O)$_2$R$^{7b}$, or R$^{7b}$S(=O)$_2$—.

3. The compound according to claim 1, wherein $R^1$ is H, D, F, Cl, Br, I, —CN, —NO$_2$, —OH, —NH$_2$, —COOH, methyl, ethyl, n-propyl, isopropyl, tert-butyl, n-butyl, trifluoromethyl, 1-chloroethyl, difluoromethyl, 2-fluoroethyl, 3,3,3-trifluoropropyl, hydroxymethyl, 1-hydroxyethyl, dihydroxymethyl, 2-hydroxyethyl, 3,3,3-trihydroxypropyl, —C(=O)R$^{7b}$, —C(=O)OR$^{7b}$, —OC(=O)R$^{7b}$, —C(=O)NR$^{8a}$R$^{8b}$, —NR$^8$C(=O)R$^{7b}$, R$^{8a}$R$^{8b}$N—S(=O)$_2$—, —R$^8$N—S(=O)$_2$R$^{7b}$, R$^{7b}$S(=O)$_2$—, $C_{6-10}$ aryl, or heteroaryl consisting of 5-10 atoms, wherein one, two, three, four or five carbon atoms of the $C_{6-10}$ aryl or heteroaryl consisting of 5-10 atoms are independently and optionally substituted with $R^{10}$;

wherein $R^{10}$ is each independently H, D, F, Cl, Br, I, —CN, —NO$_2$, —OH, —NH$_2$, —COOH, methyl, ethyl, n-propyl, isopropyl, tert-butyl, n-butyl, trifluoromethyl, 1-chloroethyl, difluoromethyl, 2-fluoroethyl, 3,3,3-trifluoropropyl, hydroxymethyl, 1-hydroxyethyl, dihydroxymethyl, 2-hydroxyethyl, 3,3,3-trihydroxypropyl, —C(=O)R$^{7b}$, —C(=O)OR$^{7b}$, —OC(=O)R$^{7b}$, —C(=O)NR$^{8a}$R$^{8b}$, —NR$^8$C(=O)R$^{7b}$, R$^{8a}$R$^{8b}$N—S(=O)$_2$—, —R$^8$N—S(=O)$_2$R$^{7b}$, or R$^{7b}$S(=O)$_2$—.

4. The compound according to claim 1, wherein $R^4$, $R^5$, and $R^6$ are each independently H, D, F, Cl, Br, I, —CN, —NO$_2$, —OH, —NH$_2$, —COOH, or $C_{1-4}$ alkyl; and wherein $R^{7a}$, $R^{7b}$, $R^{7c}$, $R^8$, $R^{8a}$, and $R^{8b}$ are each independently H, D, F, Cl, Br, I, —CN, —NO$_2$, —OH, —NH$_2$, —COOH, $C_{1-4}$ alkyl, or $C_{1-4}$ halogenated alkyl.

5. The compound according to claim 1, wherein $R^4$, $R^5$, and $R^6$ are each independently H, D, F, Cl, Br, I, —CN, —NO$_2$, —OH, —NH$_2$, —COOH, methyl, ethyl, n-propyl, isopropyl, tert-butyl, or n-butyl; and wherein $R^{7a}$, $R^{7b}$, $R^{7c}$, $R^8$, $R^{8a}$, and $R^{8b}$ are each independently H, D, F, Cl, Br, I, —CN, —NO$_2$, —OH, —NH$_2$, —COOH, methyl, ethyl, n-propyl, isopropyl, tert-butyl, n-butyl, trifluoromethyl, 1-chloroethyl, difluoromethyl, 2-fluoroethyl, or 3,3,3-trifluoropropyl.

6. The compound according to claim 4, wherein the compound is a compound represented by Formula (II-1) or (II-2); or the compound is a stereoisomer, geometric isomer, tautomer, nitrogen oxide, hydrate, solvate, or pharmaceutically acceptable salt of the compound represented by Formula (II-1) or (II-2), Formula (II-1)

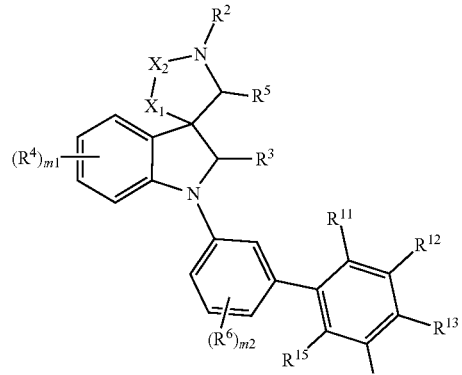

Formula (II-2)

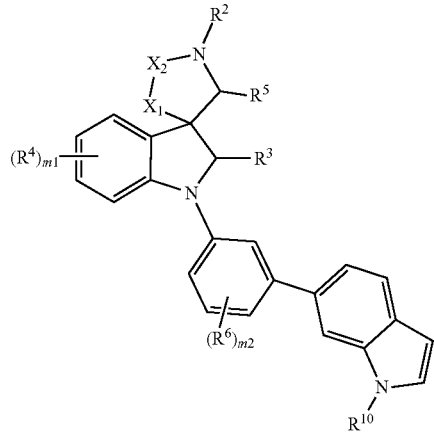

wherein $R^{11}$, $R^{12}$, $R^{13}$, $R^{14}$, or $R^{15}$ is independently H, D, F, Cl, Br, I, —CN, —NO$_2$, —OH, —NH$_2$, —COOH, C$_{1-6}$ alkyl, C$_{2-6}$ alkenyl, C$_{2-6}$ alkynyl, C$_{3-8}$ cycloalkyl, C$_{1-6}$ halogenated alkyl, C$_{1-6}$ hydroxyl-substituted alkyl, C$_{1-6}$ alkoxyl, C$_{1-6}$ halogenated alkoxyl, —C(=O)R$^{7b}$, —C(=O)OR$^{7b}$, —OC(=O)R$^{7b}$, —C(=O)NR$^{8a}$R$^{8b}$, —NR$^8$C(=O)R$^{7b}$, R$^{8a}$R$^{8b}$N—S(=O)$_2$—, —R$^8$N—S(=O)$_2$R$^{7b}$, or R$^{7b}$S(=O)$_2$—.

7. The compound according to claim 6, wherein $R^{11}$, $R^{12}$, $R^{13}$, $R^{14}$, or $R^{15}$ is independently H, D, F, Cl, Br, I, —CN, —NO$_2$, —OH, —NH$_2$, —COOH, C$_{1-4}$ alkyl, C$_{2-4}$ alkenyl, C$_{2-4}$ alkynyl, C$_{3-6}$ cycloalkyl, C$_{1-4}$ halogenated alkyl, C$_{1-4}$ hydroxyl-substituted alkyl, C$_{1-4}$ alkoxyl, C$_{1-4}$ halogenated alkoxyl, —C(=O)R$^{7b}$, —C(=O)OR$^{7b}$, —OC(=O)R$^{7b}$, —C(=O)NR$^{8a}$R$^{8b}$, —NR$^8$C(=O)R$^7$, R$^{8a}$R$^{8b}$N—S(=O)$_2$—, —R$^8$N—S(=O)$_2$R$^{7b}$, or R$^{7b}$S(=O)$_2$—.

8. The compound according to claim 6, wherein $R^{11}$, $R^{12}$, $R^{13}$, $R^{14}$, or $R^{15}$ is independently H, D, F, Cl, Br, I, —CN, —NO$_2$, —OH, —NH$_2$, —COOH, methyl, ethyl, n-propyl, isopropyl, tert-butyl, n-butyl, trifluoromethyl, 1-chloroethyl, difluoromethyl, 2-fluoroethyl, 3,3,3-trifluoropropyl, hydroxymethyl, 1-hydroxyethyl, dihydroxymethyl, 2-hydroxyethyl, 3,3,3-trihydroxypropyl, —C(=O)R$^{7b}$, —C(=O)OR$^{7b}$, —OC(=O)R$^{7b}$, —C(=O)NR$^{8a}$R$^{8b}$, —NR$^8$C(=O)R$^{7b}$, R$^{8a}$R$^{8b}$N—S(=O)$_2$—, —R$^8$N—S(=O)$_2$R$^{7b}$, or R$^{7b}$S(=O)$_2$—.

9. The compound according to claim 6, wherein the compound is a compound represented by Formula (II-1-A), (II-1-B), or (II-1-C); or the compound is a stereoisomer, geometric isomer, tautomer, nitrogen oxide, hydrate, solvate, or pharmaceutically acceptable salt of the compound represented by Formula (II-1-A), (II-1-B), or (II-1-C), (II-1-A)

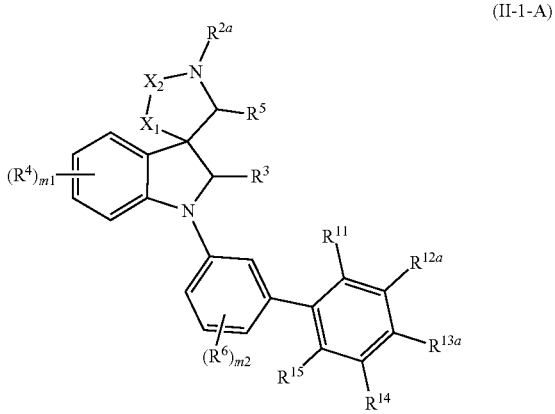

(II-1-B)

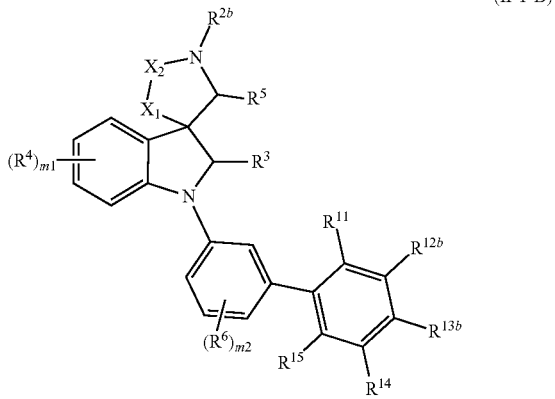

(II-1-C)

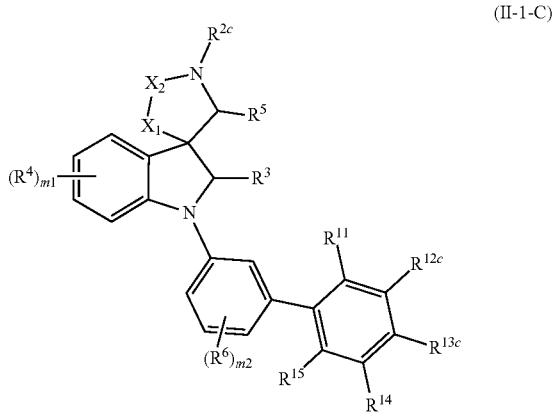

wherein $R^{2a}$ is —C(=O)R$^{7c}$, —C(=O)(C(R$^{7a}$)$_2$)$_{n1}$R$^{7c}$, —C(=O)OR$^{7c}$, —OC(=O)R$^{7c}$, or R$^{7c}$S(=O)$_2$—; $R^{12a}$ is R$^{7b}$S(=O)$_2$—; $R^{13a}$ is H, D, F, Cl, Br, I, —CN, —NO$_2$, —OH, —NH$_2$, —COOH, C$_{1-6}$ alkyl, C$_{2-6}$ alkenyl, C$_{2-6}$ alkynyl, C$_{3-8}$ cycloalkyl, C$_{1-6}$ halogenated alkyl, C$_{1-6}$ hydroxyl-substituted alkyl, C$_{1-6}$ alkoxyl, or C$_{1-6}$ halogenated alkoxy;

wherein $R^{2b}$ is $R^{7c}S(=O)_2$—; and $R^{12b}$ and $R^{13b}$ are each independently H, D, F, Cl, Br, I, —CN, —NO$_2$, —OH, —NH$_2$, —COOH, C$_{1-6}$ alkyl, C$_{2-6}$ alkenyl, C$_{2-6}$ alkynyl, C$_{3-8}$ cycloalkyl, C$_{1-6}$ halogenated alkyl, C$_{1-6}$ hydroxyl-substituted alkyl, C$_{1-6}$ alkoxyl, C$_{1-6}$ halogenated alkoxyl, —C(=O)R$^{7b}$, —C(=O)OR$^{7b}$, —OC(=O)R$^{7b}$, —C(=O)NR$^{8a}$R$^{8b}$, or —NR$^8$C(=O)R$^{7b}$; and wherein $R^{2c}$ is —C(=O)R$^{7c}$, —C(=O)(C(R$^{7a}$)$_2$)$_{n1}$R$^{7c}$, —C(=O)OR$^{7c}$, —OC(=O)R$^{7c}$, —C(=S)NR$^{8a}$R$^{8b}$, —C(=O)NR$^{8a}$R$^{8b}$, or —NR$^8$C(=O)R$^{7c}$; $R^{12c}$ is H, D, F, Cl, Br, I, —CN, —NO$_2$, —OH, —NH$_2$, —COOH, C$_{1-6}$ alkyl, C$_{2-6}$ alkenyl, C$_{2-6}$ alkynyl, C$_{3-8}$ cycloalkyl, C$_{1-6}$ halogenated alkyl, C$_{1-6}$ hydroxyl-substituted alkyl, C$_{1-6}$ alkoxyl, or C$_{1-6}$ halogenated alkoxy; and $R^{13c}$ is —C(=O)NR$^{8a}$R$^{8b}$, or —NR$^8$C(=O)R$^{7b}$.

10. The compound according to claim 9, wherein $R^{2a}$ is —C(=O)R$^{7c}$, —C(=O)(C(R$^{7a}$)$_2$)$_{n1}$R$^{7c}$, —C(=O)OR$^{7c}$, —OC(=O)R$^{7c}$, or R$^{7c}$S(=O)$_2$—; $R^{12a}$ is R$^{7b}$S(=O)$_2$—; and $R^{13a}$ is H, D, F, Cl, Br, I, —CN, —NO$_2$, —OH, —NH$_2$, —COOH, C$_{1-4}$ alkyl, C$_{2-4}$ alkenyl, C$_{2-4}$ alkynyl, C$_{3-6}$ cycloalkyl, C$_{1-4}$ halogenated alkyl, C$_{1-4}$ hydroxyl-substituted alkyl, C$_{1-4}$ alkoxyl, or C$_{1-4}$ halogenated alkoxy;

wherein $R^{2b}$ is $R^{7c}S(=O)_2$—; and $R^{12b}$ and $R^{13b}$ are each independently H, D, F, Cl, Br, I, —CN, —NO$_2$, —OH, —NH$_2$, —COOH, C$_{1-4}$ alkyl, C$_{2-4}$ alkenyl, C$_{2-4}$ alkynyl, C$_{3-6}$ cycloalkyl, C$_{1-4}$ halogenated alkyl, C$_{1-4}$ hydroxyl-substituted alkyl, C$_{1-4}$ alkoxyl, C$_{1-4}$ halogenated alkoxyl, —C(=O)R$^{7b}$, —C(=O)OR$^{7b}$, —OC(=O)R$^{7b}$, —C(=O)NR$^{8a}$R$^{8b}$, or —NR$^8$C(=O)R$^{7b}$; and wherein $R^{2c}$ is —C(=O)R$^{7c}$, —C(=O)(C(R$^{7a}$)$_2$)$_{n1}$R$^{7c}$, —C(=O)OR$^{7c}$, —OC(=O)R$^{7c}$, —C(=S)NR$^{8a}$R$^{8b}$, —C(=O)NR$^{8a}$R$^{8b}$, or —NR$^8$C(=O)R$^{7c}$; $R^{12c}$ is H, D, F, Cl, Br, I, —CN, —NO$_2$, —OH, —NH$_2$, —COOH, C$_{1-4}$ alkyl, C$_{2-4}$ alkenyl, C$_{2-4}$ alkynyl, C$_{3-6}$ cycloalkyl, C$_{1-4}$ halogenated alkyl, C$_{1-4}$ hydroxyl-substituted alkyl, C$_{1-4}$ alkoxyl, or C$_{1-4}$ halogenated alkoxy; and $R^{13c}$ is —C(=O)NR$^{8a}$R$^{8b}$, or —NR$^8$C(=O)R$^{7b}$.

11. The compound according to claim 9, wherein $R^{2a}$ is —C(=O)R$^{7c}$, —C(=O)(C(R$^{7a}$)$_2$)$_{n1}$R$^{7c}$, —C(=O)OR$^{7c}$, —OC(=O)R$^{7c}$, or R$^{7c}$S(=O)$_2$—; $R^{12a}$ is R$^{7b}$S(=O)$_2$—; and $R^{13a}$ is H, D, F, Cl, Br, I, —CN, —NO$_2$, —OH, —NH$_2$, —COOH, methyl, ethyl, n-propyl, isopropyl, tert-butyl, n-butyl, trifluoromethyl, 1-chloroethyl, difluoromethyl, 2-fluoroethyl, 3,3,3-trifluoropropyl, hydroxymethyl, 1-hydroxyethyl, dihydroxymethyl, 2-hydroxyethyl, or 3,3,3-trihydroxypropyl;

wherein $R^{2b}$ is $R^{7c}S(=O)_2$—; and $R^{12b}$ and $R^{13b}$ are each independently H, D, F, Cl, Br, I, —CN, —NO$_2$, —OH, —NH$_2$, —COOH, methyl, ethyl, n-propyl, isopropyl, tert-butyl, n-butyl, trifluoromethyl, 1-chloroethyl, difluoromethyl, 2-fluoroethyl, 3,3,3-trifluoropropyl, hydroxymethyl, 1-hydroxyethyl, dihydroxymethyl, 2-hydroxyethyl, 3,3,3-trihydroxypropyl, —C(=O)R$^{7b}$, —C(=O)OR$^{7b}$, —OC(=O)R$^{7b}$, —C(=O)NR$^{8a}$R$^{8b}$, or —NR$^8$C(=O)R$^{7b}$; and wherein $R^{2c}$ is —C(=O)R$^{7c}$, —C(=O)(C(R$^{7a}$)$_2$)$_{n1}$R$^{7c}$, —C(=O)OR$^{7c}$, —OC(=O)R$^{7c}$, —C(=S)NR$^{8a}$R$^{8b}$, —C(=O)NR$^{8a}$R$^{8b}$, or —NR$^8$C(=O)R$^{7c}$; $R^{12c}$ is H, D, F, Cl, Br, I, —CN, —NO$_2$, —OH, —NH$_2$, —COOH, methyl, ethyl, n-propyl, isopropyl, tert-butyl, n-butyl, trifluoromethyl, 1-chloroethyl, difluoromethyl, 2-fluoroethyl, 3,3,3-trifluoropropyl, hydroxymethyl, 1-hydroxyethyl, dihydroxymethyl, 2-hydroxyethyl, or 3,3,3-trihydroxypropyl; and $R^{13c}$ is —C(=O)NR$^{8a}$R$^{8b}$, or —NR$^8$C(=O)R$^{7b}$.

12. The compound according to claim 9, wherein the compound is a compound represented by Formula (II-1-A-a), (II-1-A-b), (II-1-B-a), (II-1-B-b), (II-1-C-a), or (II-1-C-b); or the compound is a stereoisomer, geometric isomer, tautomer, nitrogen oxide, hydrate, solvate, or pharmaceutically acceptable salt of the compound represented by Formula (II-1-A-a), (II-1-A-b), (II-1-B-a), (II-1-B-b), (II-1-C-a), or (II-1-C-b), (II-1-A-a)

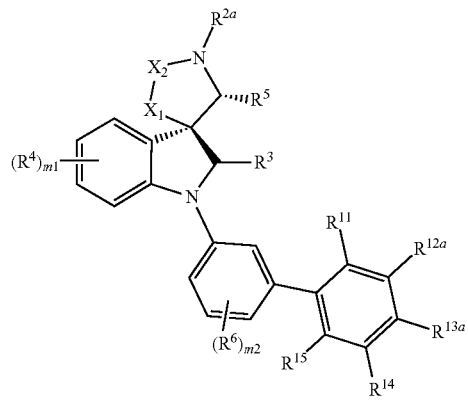

(II-1-A-b)

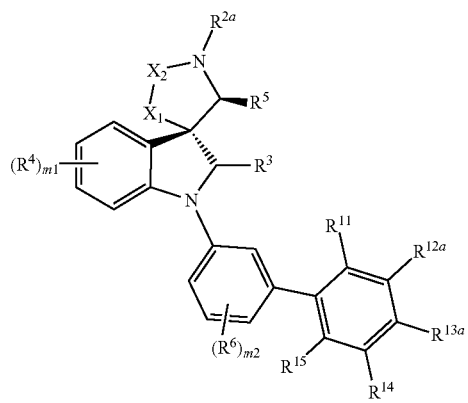

(II-1-B-a)

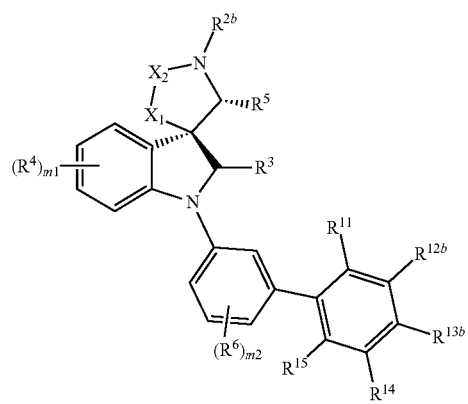

(II-1-B-b)
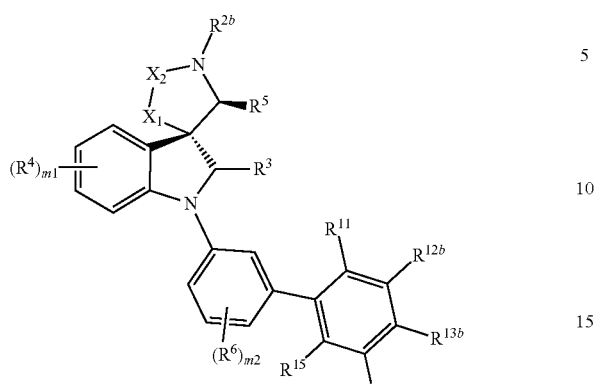
(II-1-C-a)
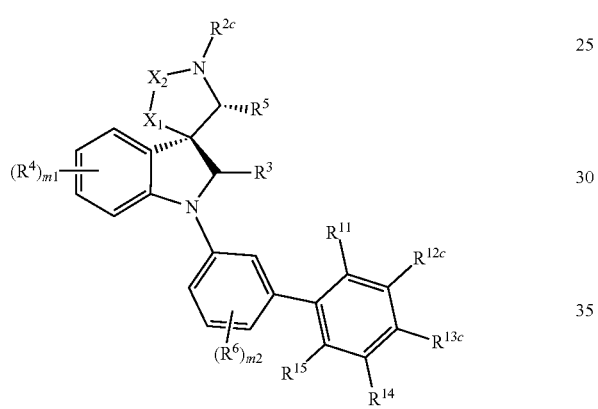
(II-1-C-b)
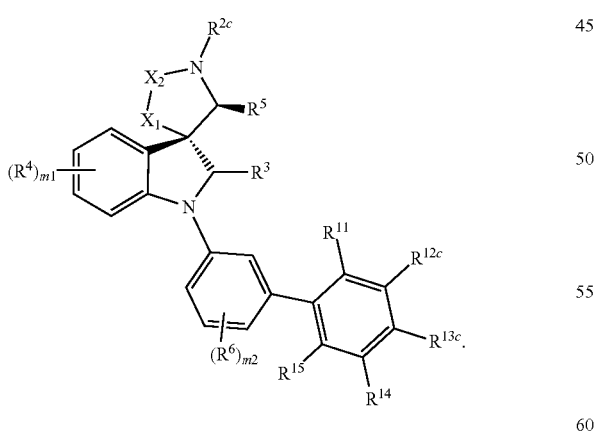
13. The compound according to claim 1, wherein the compound is a compound having one of the following structures; or the compound is a stereoisomer, geometric isomer, tautomer, nitrogen oxide, hydrate, solvate, or pharmaceutically acceptable salt of the compound having one of the following structures:
2a
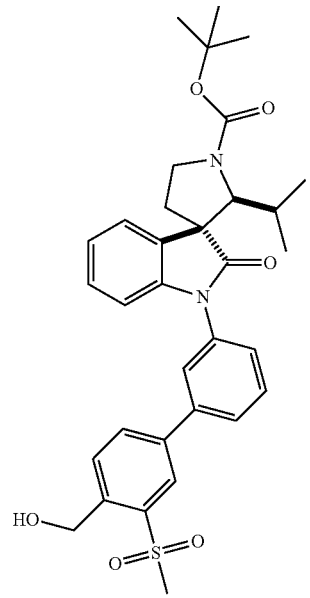
2a-1
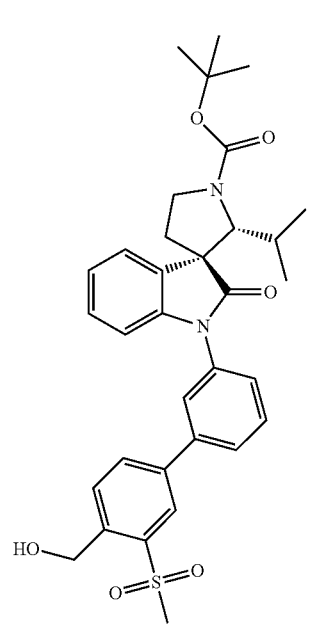

53
-continued
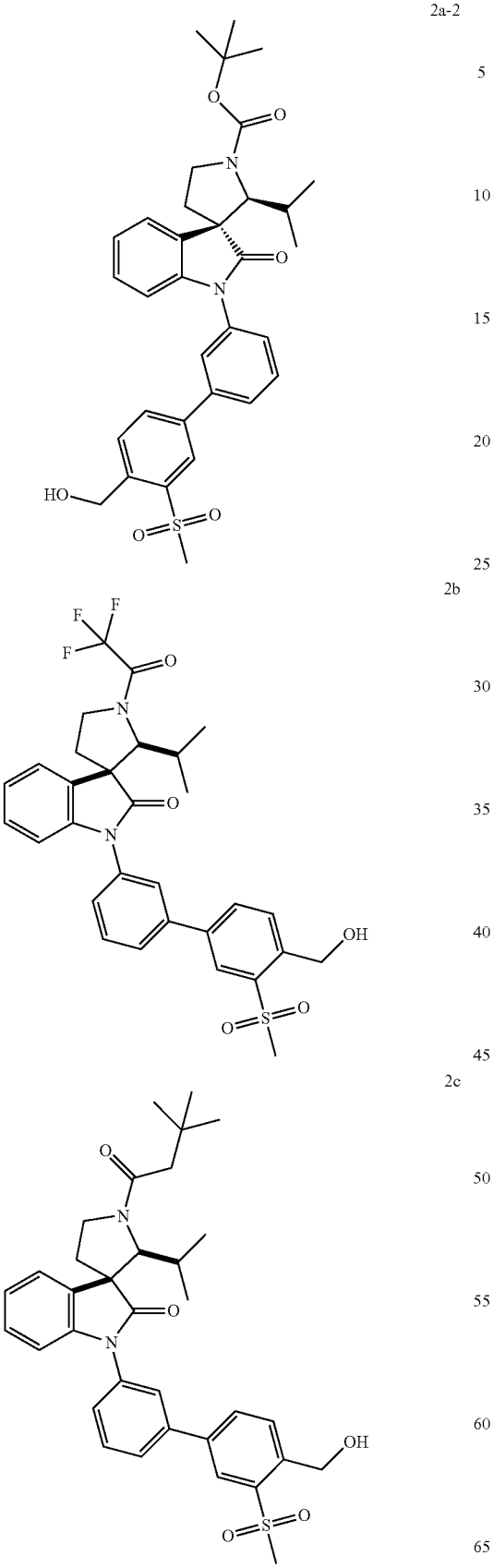
2a-2
2b
2c
54
-continued
2d
2e

55
-continued
3a
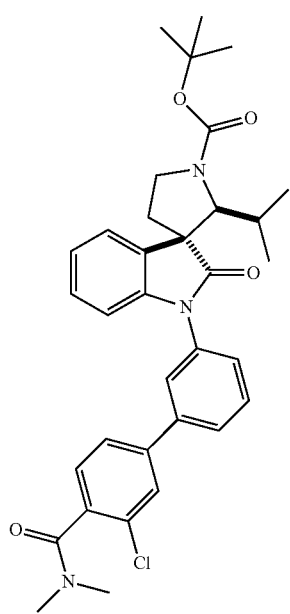
3b
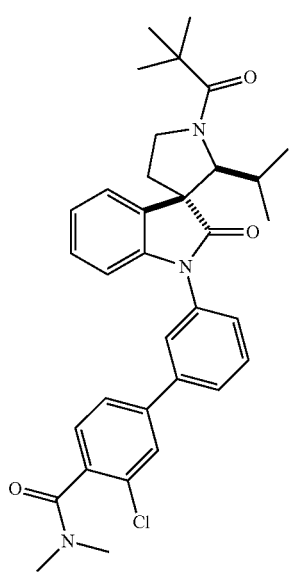
56
-continued
3c
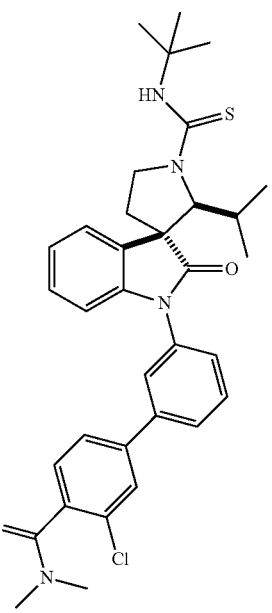
3d
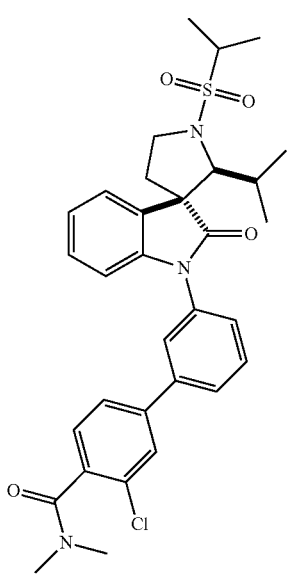

3e 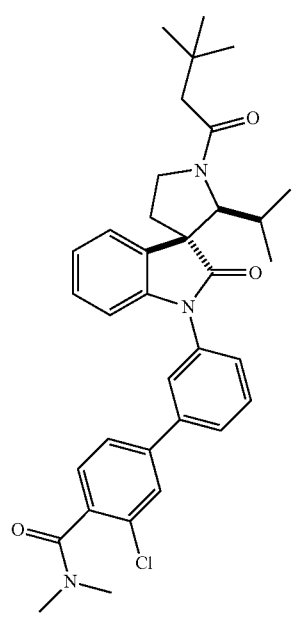
3f 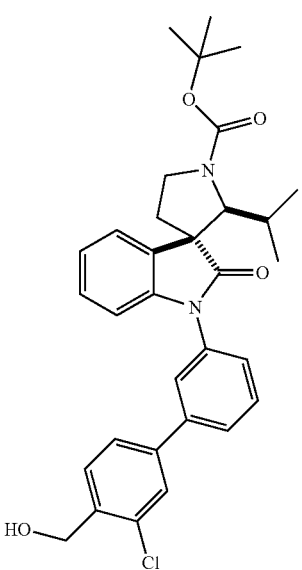
4a 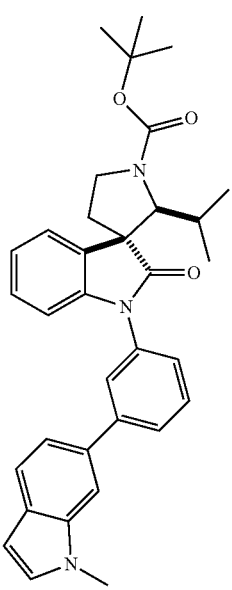
4b 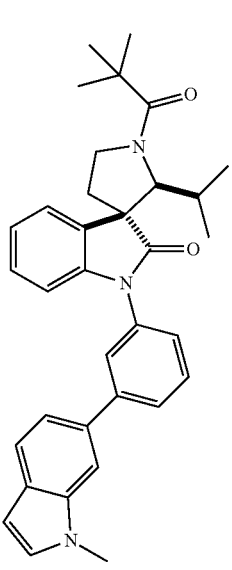

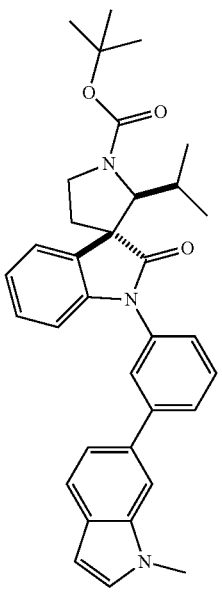

4c

14. A pharmaceutical composition, comprising the compound according to claim 1.

15. The pharmaceutical composition according to claim 14, further comprising a pharmaceutically acceptable carrier, excipient, diluent, adjuvant, vehicle, or any combinations thereof.

16. The pharmaceutical composition according to claim 14, further comprising an additional therapeutic agent,
wherein the additional therapeutic agent is optionally a medicament for treatment of hyperlipidemia, fatty liver, obesity, diabetes, metabolic syndrome, or a combination thereof; and wherein the additional therapeutic agent is optionally a medicament for treatment of glioblastoma, atherosclerosis, dyslipidemia, metabolic syndrome, Parkinson's disease, Alzheimer's disease, multiple sclerosis, atopic dermatitis, rheumatoid arthritis, osteoporosis, or a combination thereof.

17. The pharmaceutical composition according to claim 16, wherein the medicament for the treatment of hyperlipidemia, fatty liver, obesity, diabetes or metabolic syndrome is atorvastatin, gemfibrozil, acpimox, Eicosapentaenoic acid, metformin, glimepiride, repaglinide, empagliflozin, or any combination thereof; and optionally, the medicament for the treatment of glioblastoma, atherosclerosis, dyslipidemia, metabolic syndrome, Parkinson's disease, Alzheimer's disease, multiple sclerosis, atopic dermatitis, rheumatoid arthritis or osteoporosis is temozolomide, fotemustine, statin, fibrate, trihexyphenidyl, aspirin, non-steroidal anti-inflammatory medicament, or any combination thereof, preferably, the statin is lovastatin or simvastatin; the fibrate is clofibrate, lifibrate, or bezafibrate; and the non-steroidal anti-inflammatory medicament is diclofenac, nabumetone, or meloxicam.

18. A method for treating a disease, comprising:

administering the compound according to claim 1 to a patient, wherein the disease comprises at least one selected from hyperlipidemia, fatty liver, obesity, diabetes, metabolic syndrome, glioblastoma, atherosclerosis, dyslipidemia, metabolic syndrome, Parkinson's disease, Alzheimer's disease, multiple sclerosis, atopic dermatitis, rheumatoid arthritis, and osteoporosis.

\* \* \* \* \*